US007261857B2

(12) United States Patent
Suslick et al.

(10) Patent No.: US 7,261,857 B2
(45) Date of Patent: *Aug. 28, 2007

(54) COLORIMETRIC ARTIFICIAL NOSE HAVING AN ARRAY OF DYES AND METHOD FOR ARTIFICIAL OLFACTION

(75) Inventors: Kenneth S. Suslick, Champaign, IL (US); Neal A. Rakow, Champaign, IL (US); Avijit Sen, Urbana, IL (US); William B. McNamara, III, Urbana, IL (US); Margaret E. Kosal, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 534 days.

This patent is subject to a terminal disclaimer.

(21) Appl. No.: 10/279,788

(22) Filed: Oct. 24, 2002

(65) Prior Publication Data

US 2003/0143112 A1 Jul. 31, 2003

Related U.S. Application Data

(63) Continuation-in-part of application No. 09/705,329, filed on Nov. 3, 2000, now Pat. No. 6,495,102, which is a continuation-in-part of application No. 09/532,125, filed on Mar. 21, 2000, now Pat. No. 6,368,558.

(51) Int. Cl.
*G01N 21/00* (2006.01)

(52) U.S. Cl. .................... 422/55; 422/68.1; 422/82.05; 422/83; 422/85; 436/164; 436/172

(58) Field of Classification Search .................. 422/55, 422/68.1, 82.05–82.11, 83, 85, 86; 436/164, 436/165, 172
See application file for complete search history.

(56) References Cited

U.S. PATENT DOCUMENTS 4,759,210 A 7/1988 Wohltjen (Continued)

FOREIGN PATENT DOCUMENTS

EP 0352610 A2 1/1990

OTHER PUBLICATIONS

Krishna Persaud & George Dodd, "Analysis of Discrimination Mechanisms in the Mammalian Olfactory System using a Model Nose," Nature vol. 299, Sep. 23, 1982, pp. 352-355.

(Continued)

*Primary Examiner*—Jill Warden
*Assistant Examiner*—Dwayne K. Handy
(74) *Attorney, Agent, or Firm*—Licata & Tyrrell P.C.

(57) ABSTRACT

The present invention involves an artificial nose having an array comprising at least a first dye and a second dye in combination and having a distinct spectral response to an analyte. In one embodiment, the first and second dyes are from the group comprising chemoresponsive dyes, and the second dye is distinct from the first dye. In one embodiment, the first dye is selected from the group consisting of porphyrin, chlorin, chlorophyll, phthalocyanine, and salen, or their metal complexes. In another embodiment, the second dye is selected from the group of dyes consisting of acid-base indicator dyes and solvatochromic dyes. The present invention is particularly useful in detecting metal ligating vapors. Further, the array of the present invention can be connected to a visual display device.

22 Claims, 21 Drawing Sheets
(13 of 21 Drawing Sheet(s) Filed in Color)

U.S. PATENT DOCUMENTS

| | | | |
|---|---|---|---|
| 4,907,441 | A | 3/1990 | Shurmer |
| 5,489,988 | A | 2/1996 | Ackley et al. |
| 5,512,490 | A | 4/1996 | Walt et al. |
| 5,733,506 | A | 3/1998 | Silver et al. |
| 5,786,219 | A | 7/1998 | Zhang et al. |
| 5,814,524 | A | 9/1998 | Walt et al. |
| 5,834,626 | A | 11/1998 | De Castro et al. |
| 5,863,460 | A | 1/1999 | Slovacek et al. |
| 5,952,237 | A | 9/1999 | Tanaka et al. |
| 5,955,603 | A | 9/1999 | Therien et al. |
| 5,994,150 | A | 11/1999 | Challener et al. |
| 6,078,705 | A | 6/2000 | Neuschafer et al. |
| 6,140,138 | A | 10/2000 | Bard et al. |
| 6,210,910 | B1 * | 4/2001 | Walt et al. .................. 435/7.32 |
| 6,331,438 | B1 * | 12/2001 | Aylott et al. ................. 436/172 |
| 6,368,558 | B1 | 4/2002 | Suslick et al. |
| 6,387,709 | B1 * | 5/2002 | Mason et al. ................ 436/164 |
| 6,395,558 | B1 * | 5/2002 | Duveneck et al. ........... 436/172 |
| 6,429,027 | B1 * | 8/2002 | Chee et al. ................... 436/518 |
| 6,490,030 | B1 * | 12/2002 | Gill et al. ...................... 356/71 |
| 6,492,182 | B1 * | 12/2002 | Bright et al. ................. 436/172 |
| 6,495,102 | B1 * | 12/2002 | Suslick et al. ................ 422/55 |
| 6,512,580 | B1 * | 1/2003 | Behringer et al. ........... 356/244 |
| 6,649,416 | B1 * | 11/2003 | Kauer et al. ................. 436/164 |
| 6,713,260 | B2 * | 3/2004 | Tomich et al. ................. 435/6 |
| 6,859,570 | B2 * | 2/2005 | Walt et al. ..................... 385/12 |

OTHER PUBLICATIONS

Janet Kavandi, James Callis, Martin Gouterman, Gamai Khalil, Daniel Wright, "Luminescent Barometry in Wind Tunnels," *Rev. Sci. Instrum*, vol. 61, No. 11, Nov. 1990, pp. 3340-3347.

Jay W. Grate and Michael H. Abraham, "Solubility Interactions and the Design of Chemically Selective Sorbent Coatings for Chemical Sensors and Arrays," *Sensors and Actuators* B, 3 (1991) pp. 85-111.

Julian W. Gardner, Harold V. Shurmer and Paul Corcoran, "Integrated Tin Oxide Odour Sensors," *Sensors and Actuators* B, 4 (1991) pp. 117-121.

J. W. Gardner, H. V. Shurmer, and T. T. Tan, "Application of an Electronic Nose to the Discrimination of Coffees," *Sensors and Actuators* B, 6 (1992) pp. 71-75.

Alan E. Baron, J.D.S. Danielson, Martin Gouterman, Jiang River Wan, "Submillisecond Response Times of Oxygen-Quenched Luminescent Coatings," *Rev. Sci. Instrum*. 64 (12) Dec. 1993, pp. 3394-3402.

Weekey Wai-San Lee, Kwok-Yin Wong, Xiang-Ming Li, Yiu-Bong Leung, Chi-Shing Chan and Kin Shing Chan, Halogenated Platinum Porphyrins as Sensing Materials for Luminescence-Based Oxygen Sensors, *J. Mater. Chem.* 1993, pp. 1031-1035.

Julian W. Gardner and Philip N. Bartlett, "A Brief History of Electronic Noses," *Sensors and Actuators* B, 18-19 (1994), pp. 211-220.

Michael S. Freund and Nathan S. Lewis, "A Chemically Diverse Conducting Polymer-Based Electronic Nose," *Proc. Natl. Acad. Sci. USA*, Mar. 1995, vol. 92, pp. 2652-2656.

Andrea E. Hoyt and Antonio J. Ricco, "Speciation of Linear and Branched Hydrocarbons by a Fluorinated Polyimide Film-Based Surface Acoustic Wave Sensor," *J. Am. Chem. Soc.* 1995, 117, pp. 8672-8673.

Todd A. Dickinson, Joel White, John S. Kauer and David R. Walt, "A Chemical-Detecting System Based on a Cross-Reactive Optical Sensory Array," *Nature*, vol. 382, Aug. 22, 1996, pp. 697-700.

Andrew A. Vaughan, Mark G. Baron and Ramaier Narayanaswamy, "Optical Ammonia Sensing Films Based on an Immobilized Metalloporphyrin," *Analytical Communications*, Nov. 1996, vol. 33, pp. 393-396.

J.A.J. Brunink, et al., "The Application of Metalloporphyrins as Coating Material for Quartz Microbalance-Based Chemical Sensors," *Analytica Chimica ACTA*, 325 (1996) pp. 53-64.

Brett J. Doleman, Robert D. Sanner, Erik J. Severin, Robert H. Grubbs, and Nathan S. Lewis, "Use of Compatible Polymer Blends to Fabricate Arrays of Carbon Black-Polymer Composite Vapor Detectors," *Analytical Chemistry*, vol. 70, No. 13, Jul. 1, 1998, pp. 2560-2564.

Richard M. Crooks and Antonio J. Ricco, "New Organic Materials Suitable for Use in Chemical Sensor Arrays," *Accounts of Chemical Research*, vol. 31, No. 5, 1998, pp. 219-227.

Gregory A. Sotzing, Jennifer N. Phend, Robert H. Grubbs and Nathan S. Lewis, "Highly Sensitive Detection and Discrimination of Biogenic Amines Utilizing Arrays of Polyaniline/Carbon Black Composite Vapor Detectors," *Chem. Mater.* 2000, vol. 12, published on Web Feb. 29, 2000, pp. 593-595.

Todd A. Dickinson, Karri L. Michael, John S. Kauer and David R. Walt, "Convergent, Self-Encoded Bead Sensor Arrays in the Design of an Artificial Nose," *Anal. Chem.* 1999, vol. 71, Jun. 1, 1999, pp. 2192-2198.

M.G. Baron, R. Narayanaswamy, S.C. Thorpe, "Hydrophobic Membrane Sensors for the Optical Determination of Hydrogen Chloride Gas," *Sensors and Actuators* B 34 (1996), pp. 511-515.

Tanaka, et al., Abstract, "Gas-Sensitive Colorants, Gas Sensors and Apparatus and Method for Detecting Gas," Copyright 1999 ACS.

Suslick, K. S. & Van Deusen-Jeffries, S. in "Comprehensive Supramolecular Chemistry" (ed. Lehn, J.M.) 141-170 (Elsevier Science, Ltd., Oxford, 1996).

Adler, A. D. et al. "A Simplified Synthesis for meso-Tetraphenylporphin," *J. Org. Chem.* 32, 476 (1967).

Sen, A. & Suslick, K.S. "Shape Selective Discrimination of Small Organic Molecules," *J. Am. Chem. Soc.*, 1-9, p. S.1 and 2 (In the press).

Chou, J.-H., Nalwa, H.S., Kosal, M. E., Rakow, N.A. & Suslick, K.S., "Applications of Porphyrins and Metalloporphyrins to Materials Chemistry," From *The Porphyrin Handbook* (eds. Kadish, K., Smith, K., & Guilard, R.) p. 43-132 (Academic Press, New York, 2000).

Heilig, A. et al., "Gas Identification by Modulating Temperatures of $SnO_2$-Based Thick Film Sensors," Sensor and Actuators B 43, 45-51 (1997).

Bhyrappa, P., Vaijayanthimala, G. & Suslick, K.S. "Shape-Selective Litigation to Dendrimer-Metalloporphyrins," *J. Am. Chem. Soc.* 121, 262-263 (1999).

Bhyrappa, P., Young, J.K., Moore, J.S. and Suslick, K.S. "Dendrimer-Metalloporphyrins: Synthesis and Catalysis," *J. Am. Chem. Soc.* 118, 5708-5711 (1996).

Datta-Gupta, N. & Bardos, T. J. "Synthetic Porphyrins II: Preparation and Spectra of Some Metal Chelates of para-Substituted-meso-Tetraphenylporphines," *J. Pharm. Sci.*, 57, 300-304 (1968).

Nappa, M. & Valentine, J.S. "The Influence of Axial Ligands on Metalloporphyrin Visible Absorption Spectra. Complexes of Tetraphenylporphinatozinc," *J. Am. Chem. Soc.* 100, 5075-5080 (1978).

Barley, M., Becker, J. Y., Domazetis, G., Dolphin, D. & James, B. R. "Synthesis and Redox Chemistry of Octaethylporphyrin Complexes of Ruthenium (II) and Ruthenium (III)", *Can. J. Chem.*, 61, 2389-2396 (1983).

Adler, A. D., Longo, F. R., Kampas, F. & Kim, J. "On the Preparation of Metalloporphyrins," *J. Inorg. Nucl. Chem.* 32, 2443-2445 (1970).

Di Natale, C. et al. "The Exploitation of Metalloporphyrins as Chemically Interactive Material in Chemical Sensors," *Materials Science & Engineering* C5, 209-215 (1998).

Walt, D. R. "Fiber Optic Imaging Sensors," *Acc. Chem. Res.* 31, 267-278 (1998).

Lonergan, M.C. et al. "Array-Based Vapor Sensing Using Chemically Sensitive, Carbon Black-Polymer Resistors," *Chem. Mater* 8, 2298-2312 (1996).

Axel, R. "The Molecular Logic of Smell," *Science Am.* 273, 154-159 (1995).

Lancet, D. & Ben-Arie, N. "Olfactory Receptors," *Curr. Biol.* 3, 668-674 (1993).

Dryer, L. & Berghard A. "Odorant Receptors: A Plethora of G-Protein-Coupled Receptors," *Trends Pharmacol. Sci.* 20, 413-417 (1999).

Gelperin, A., Flores, J., Raccuia-Behling, F., Cooke, I.R.C., "Nitric Oxide and Carbon Monoxide Modulate Oscillations of Olfactory Interneurons in a Terrestrial Mollusk," *J. Neurophysiol.* 83, 116-127 (2000).

Holten, D., and Gouterman, M., "Transient Absorption Spectra and Excited Kinetics of Transition Metal Porphyrins," *Optical Properties and Structure of Tetrapyrroles*, pp. 63-90 (Blauer, G. & Sund, H. (eds), Walter de Gruyter & Co., Berlin, 1985).

Yaws, C. L., Handbook of Vapor Pressure (Gulf, Houston, 1994), copy not enclosed.

Suslick, K.S.; Reinert, T. J., The Synthetic Analogs of $O_2$—Binding Heme Proteins; Chem Ed. 1985, vol. 62, pp. 974-982.

Collman, J. P.; Zhang, X.; Lee, V. J.; Uffelman, E. S.; Brauman, J. I., "Regioselective and Enantioselective Epoxidation Catalyzed by Metalloporphyrins," Science 1993, vol. 261, pp. 1401-1411.

Collman, J. P.; Zhang, X. in Comprehensive Supramolecular Chemistry, "Functional Analogues of the Oxygen Binding and Activating Heme Proteins," pp. 1-32.

Suslick, K.S.; van Deusen-Jeffries, S.; "Biomimetic Shape-Selective Oxidations," vol. 5, pp. 1-30.

Suslick, K. S. in Activation and Functionalization of Alkanes; "Shape-Selective Oxidation of Hydrocarbons," Hill, C. L., ed.; Wiley & Sons: New York, 1989; pp. 219-241.

Sheldon, R. A. Ed. Marcel Dekker, Metalloporphyrins in Catalytic Oxidations;: New York, 1994, cover page and pp. ii though x.

Bampos, N.; Marvaud, V., Sanders, J. K. M., "Metalloporphyrin Oligomers with Collapsible Cavities: Characterisation and Recognition Properties of Individual Atropisomers," Chem. Eur. J. 1998, vol. 4, No. 2, pp. 335-343.

Stibrany, R. T.; Vasudevan, J.; Knapp, S.; Potenza, J. A.; Emge, T.; Schugar, H. J., "Two Modes of Self-Coordinating Edge-over-Edge Zn(II) Porphyrin Dimerization: A Structural and Spectroscopic Comparison," J. Am. Chem. Soc. 1996, vol. 118, pp. 3980-3981.

Bhyrappa, P.; Vaijayanthimala, G.; Suslick, K. S., "Shape-Selective Ligation to Dendrimer-Metalloporphyrins," J. Am. Chem. Soc. 1999, vol. 121, pp. 262-263.

Imai, H.; Nakagawa, S.; Kyuno, E., "Recognition of Axial Ligands by a Zinc Porphyrin Host on the Basis of Nonpolar Interligand Interaction," J. Am. Chem. Soc. 1992, vol. 114, pp. 6719-6723.

Momenteau, M.; Mispelter, J.; Loock, B.; Bisagni, E., "Both-faces Hindered Porphyrins. Part 1. Synthesis and Characterization of Basket-handle Porphyrins and Their Iron Complexes," J. Chem. Soc. Perkin Trans. 1, 1983, pp. 189-196.

Lindsey, J. S.; Wagner, R. W., "Investigation of the Synthesis of Ortho-Substituted Tetraphenylporphyrins," J. Org. Chem. 1989, vol. 54, pp. 828-836.

Corey. E. J: Venkateswarlu, A., "Protection of Hydroxyl Groups as *tert*-Butyldimethylsilyl Derivatives," J. Am. Chem. Soc. 1972, vol. 94:17, pp. 6190-6191.

Collman, J. P.; Brauman, J. I.; Doxsee, K. M.; Halbert, T. R.; Hayes, S. E.; Suslick, K. S., "Oxygen Binding to Cobalt Porphyrins," J. Am. Chem. Soc. 1978, vol. 100, pp. 2761-2766.

Suslick, K. S.; Fox, M. M.; Reinert, T., "Influences on CO and $O_2$ Binding to Iron(II) Porphyrins," J. Am. Chem. Soc. 1984, vol. 106, pp. 4522-4525.

Suslick, K. S.; Cook, B. R., "Regioselective Epoxidations of Dienes with Manganese(III) Porphyrin Catalysts," J. Chem. Soc., Chem. Comm. 1987, pp. 200-202.

Cook, B. R.; Reinert, T. J.; Suslick, K. S., "Shape Selective Alkane Hydroxylation by Metalloporphyrin Catalysts," J. Am. Chem. Soc. 1986, vol. 108, pp. 7281-7286.

Suslick, K. S.; Cook, B. R.; Fox, M. M., "Shape-selective Alkane Hydroxylation," J. Chem. Soc., Chem. Comm. 1985, pp. 580-582.

Suslick, K. S.; Fox, M. M., "A Bis-Pocket Porphyrin," J. Am. Chem. Soc., 1983, vol. 105, pp. 3507-3510.

Patent Abstracts of Japan; Publication No. 63234137; Publication Date: Sep. 29, 1988.

Patent Abstracts of Japan; Publication No. 63234138; Publication Date: Sep. 29, 1988.

* cited by examiner

M(TPP)

| Metal | Z/r Ratio (Å⁻¹) |
| --- | --- |
| $Sn^{4+}$ | 5.80 |
| $Co^{3+}$ | 5.50 |
| $Cr^{3+}$ | 4.88 |
| $Mn^{3+}$ | 4.65 |
| $Fe^{3+}$ | 4.65 |
| $Co^{2+}$ | 3.08 |
| $Cu^{2+}$ | 2.74 |
| $Ru^{2+}$ | 2.71 |
| $Zn^{2+}$ | 2.70 |
| $Ag^{2+}$ | 2.13 |

$Sn^{4+}$ $Co^{3+}$ $Cr^{3+}$ $Mn^{3+}$ $Fe^{3+}$ $Co^{2+}$ $Cu^{2+}$ $Ru^{2+}$ $Zn^{2+}$ $Ag^{2+}$ $2H^+$
(FB)

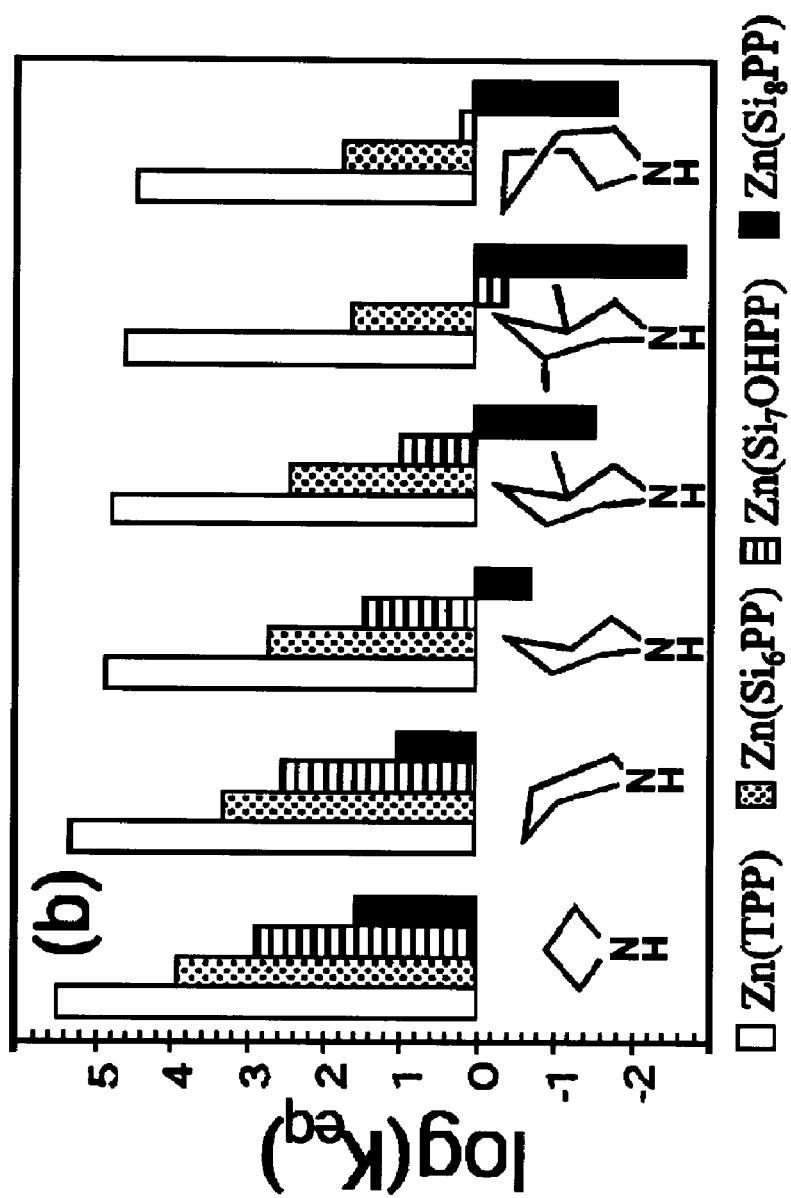

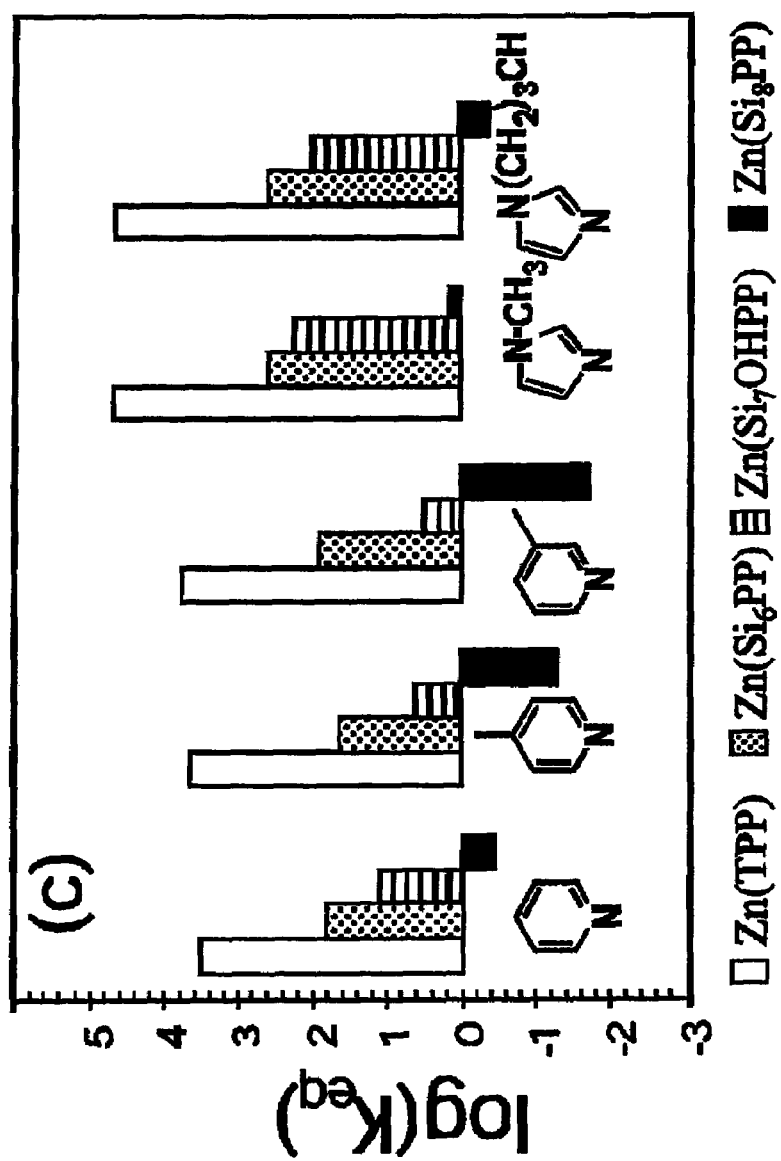

COLORIMETRIC ARTIFICIAL NOSE HAVING AN ARRAY OF DYES AND METHOD FOR ARTIFICIAL OLFACTION

CONTINUING APPLICATION DATA

This application is a Continuation-in-Part of U.S. application Ser. No. 09/705,329, filed on Nov. 3, 2000, now U.S. Pat. No. 6,495,102, which is a Continuation-in-Part of U.S. application Ser. No. 09/532,125, filed on Mar. 21, 2000, now U.S. Pat. No. 6,368,558.

This invention was made with Government support under Contract Nos. HL25934 awarded by the National Institutes of Health & Contract No. DAAG55-97-1-2211 awarded by the Department of the Army. The Government has certain rights in the invention.

FIELD OF THE INVENTION

The present invention relates to methods and apparatus for artificial olfaction, e.g., artificial noses, for the detection of odorants by a visual display.

BACKGROUND OF THE INVENTION

There is a great need for olfactory or vapor-selective detectors (i.e., "artificial noses") in a wide variety of applications. For example, there is a need for artificial noses that can detect low levels of odorants and/or where odorants may be harmful to humans, animals or plants. Artificial noses that can detect many different chemicals are desirable for personal dosimeters in order to detect the type and amount of odorants exposed to a human, the presence of chemical poisons or toxins, the spoilage in foods, the presence of flavorings, or the presence of vapor emitting items, such as plant materials, fruits and vegetables, e.g., at customs portals.

Conventional artificial noses have severe limitations and disadvantages and are not considered generally useful for such purposes. Limitations and disadvantages of conventional artificial noses include their need for extensive signal transduction hardware, and their inability to selectively target metal-coordinating vapors and toxins. In addition, artificial noses which incorporate mass sensitive signal transduction or polar polymers as sensor elements are susceptible to interference by water vapor. This limitation is significant in that it can cause variable response of the detector with changes ambient humidity. See F. L. Dickert, O. Hayden, Zenkel, M. E. *Anal. Chem.* 71, 1338 (1999).

Initial work in the field of artificial noses was conducted by Wilkens and Hatman in 1964, though the bulk of research done in this area has been carried out since the early 1980's. See, e.g., W. F. Wilkens, A. D. Hatman. *Ann. NY Acad. Sci.*, 116, 608 (1964); K. Pursaud, G. H. Dodd. *Nature,* 299, 352-355 (1982); and J. W. Gardner, P. N. Bartlett. *Sensors and Actuators B,* 18-19, 211-220 (1994).

Vapor-selective detectors or "artificial noses" are typically based upon the production of an interpretable signal or display upon exposure to a vapor emitting substance or odorant (hereinafter sometimes referred to as an "analyte"). More specifically, typical artificial noses are based upon selective chemical binding or an interface between a detecting compound of the artificial nose and an analyte or odorant, and then transforming that chemical binding into a signal or display, i.e., signal transduction.

Polymer arrays having a single dye have been used for artificial noses. That is, a series of chemically-diverse polymers or polymer blends are chosen so that their composite response distinguishes a given odorant or analyte from others. Examples of polymer array vapor detectors, including conductive polymer and conductive polymer/carbon black composites, are discussed in: M. S. Freund, N. S. Lewis, *Proc. Natl. Acad. Sci. USA* 92, 2652-2656 (1995); B. J. Doleman, R. D. Sanner, E. J. Severin, R. H. Grubbs, N. S. Lewis, *Anal. Chem.* 70, 2560-2564 (1998); T. A. Dickinson, J. White, J. S. Kauer, D. R. Walt, *Nature* 382, 697-700 (1996)(polymer array with optical detection); A. E. Hoyt, A. J. Ricco, H. C. Yang, R. M. Crooks, *J. Am. Chem. Soc.* 117, 8672 (1995); and J. W. Grate, M. H. Abraham, *Sensors and Actuators B* 3, 85-111 (1991).

Other interface materials include functionalized self-assembled monolayers (SAM), metal oxides, and dendrimers. Signal transduction is commonly achieved with mass sensitive piezoelectric substrates, surface acoustic wave (SAW) transducers, or conductive materials. Optical transducers (based on absorbance or luminescence) have also been examined. Examples of metal oxide, SAM, and dendrimer-based detectors are discussed in J. W. Gardner, H. V. Shurmer, P. Corcoran, *Sensors and Actuators B* 4, 117-121 (1991); J. W. Gardner, H. V. Shurmer, T. T. Tan, *Sensors and Actuators B* 6, 71-75 (1992); and R. M. Crooks, A. J. Ricco, *Acc. Chem. Res.* 31, 219-227 (1998). These devices also use a single dye.

Techniques have also been developed using a metalloporphyrin for optical detection of a specific, single gas such as oxygen or ammonia, and for vapor detection by chemically interactive layers on quartz crystal microbalances. See A. E. Baron, J. D. S. Danielson, M. Gouterman, J. R. Wan, J. B. Callis, *Rev. Sci. Instrum.* 64, 3394-3402 (1993); J. Kavandi, et al., *Rev. Sci. Instrum.* 61, 3340-3347 (1990); W. Lee, et al., *J. Mater. Chem.* 3, 1031-1035 (1993); A. A. Vaughan, M. G. Baron, R. Narayanaswamy, *Anal Comm.* 33, 393-396 (1996); J. A. J. Brunink, et al., *Anal. Chim. Acta* 325, 53-64 (1996); C. Di Natale, et al., *Sensors and Actuators B* 44, 521-526 (1997); and C. DiNatale, et al., *Mat. Sci. Eng. C* 5, 209-215 (1998). However, these techniques either require extensive signal transduction hardware, or, as noted above, are limited to the detection of a specific, single gas. They are also subject to water vapor interference problems, as discussed previously.

While typical systems to date have demonstrated some success in chemical vapor detection and differentiation, these systems have focused on the detection of non-metal binding or non-metal ligating solvent vapors, such as arenes, halocarbons and ketones. Detection of metal-ligating vapors (such as amines, thiols, and phosphines) has been much less explored. Further, while some single porphyrin based sensors have been used for detection of a single strong acid, there is a need for sensor devices that will detect a wide variety of vapors.

To summarize, there are a number of limitations and drawbacks to typical artificial noses and single porphyrin based sensors. As noted above typical artificial noses are not designed for metal binding and metal ligating vapors, such as amines, thiols, and phosphines. Further, typical artificial noses require extensive signal transduction hardware, and are subject to interference from water vapor. As noted above, single porphyrin based sensors have been used for detection of a single strong acid, but cannot detect a wide variety of vapors. Thus, there is a need for new artificial noses and methods that overcome these and other limitations of prior artificial noses and single porphyrin based sensors and methods.

SUMMARY OF THE INVENTION

The present invention comprises an array of dyes including at least a first dye and a second dye which in combination provide a spectral response distinct to an analyte or odorant. The dyes of the present invention produce a response in the spectrum range of about 200 nanometers to 2,000 nanometers, which includes the visible spectrum of light. It has now been discovered that an array of two or more dyes responds to a given ligating species with a unique color pattern spectrally and in a time dependent manner. Thus, dyes in the array of the present invention are capable of changing color in a distinct manner when exposed to any one analyte or odorant. The pattern of colors manifested by the multiple dyes is indicative of a specific or given analyte. In other words, the pattern of dye colors observed is indicative of a particular vapor or liquid species.

In a preferred embodiment, the dyes of the array are porphyrins. In another preferred embodiment, the porphyrin dyes are metalloporphyrins. In a further preferred embodiment, the array will comprise ten to fifteen distinct metalloporphyrins in combination. Metalloporphyrins are preferable dyes in the present invention because they can coordinate metal-ligating vapors through open axial coordination sites, and they produce large spectral shifts upon binding of or interaction with metal-ligating vapors. In addition, porphyrins, metalloporphyrins, and many dyes show significant color changes upon changes in the polarity of their environment; this so-called solvatochromic effect will give net color changes even in the absence of direct bonding between the vapor molecules and the metal ions. Thus, metalloporphyrins produce intense and distinctive changes in coloration upon ligand binding with metal ligating vapors.

The present invention provides a means for the detection or differentiation and quantitative measurement of a wide range of ligand vapors, such as amines, alcohols, and thiols. Further, the color data obtained using the arrays of the present innovation may be used to give a qualitative fingerprint of an analyte, or may be quantitatively analyzed to allow for automated pattern recognition and/or determination of analyte concentration. Because porphyrins also exhibit wavelength and intensity changes in their absorption bands with varying solvent polarity, weakly ligating vapors (e.g., arenes, halocarbons, or ketones) are also differentiable.

Diversity within the metalloporphyrin array may be obtained by variation of the parent porphyrin, the porphyrin metal center, or the peripheral porphyrin substituents. The parent porphyrin is also referred to as a free base ("FB") porphyrin, which has two central nitrogen atoms protonated (i.e., hydrogen cations bonded to two of the central pyrrole nitrogen atoms). A preferred parent porphyrin is depicted in FIG. 2A, with the substitution of a two hydrogen ion for the metal ion (depicted as "M") in the center of the porphyrin. In FIG. 2A, TTP stands for 5,10,15,20-tetraphenylporphyrinate(-2).

In accordance with the present invention, calorimetric difference maps can be generated by subtracting unexposed and exposed metalloporphyrin array images (obtained, for example, with a common flatbed scanner or inexpensive video or charge coupled device ("CCD") detector) with image analysis software. This eliminates the need for extensive and expensive signal transduction hardware associated with previous techniques (e.g., piezoelectric or semiconductor sensors). By simply differencing images of the array before and after exposure to analytes, the present invention provides unique color change signatures for the analytes, for both qualitative recognition and quantitative analysis.

Sensor plates which incorporate vapor sensitive combinations of dyes comprise an embodiment of the present invention which is economical, disposable, and can be utilized to provide qualitative and/or quantitative identification of an analyte. In accordance with the present invention, a catalog of arrays and the resultant visual pattern for each analyte can be coded and placed in a look-up table or book for future reference. Thus, the present invention includes a method of detecting an analyte comprising the steps of forming an array of at least a first dye and a second dye, subjecting the array to an analyte, inspecting the first and second dyes for a spectral response, and comparing the spectral response with a catalog of analyte spectral responses to identify the analyte.

Because sensing is based upon either covalent interaction (i.e., ligation) or non-covalent solvation interactions between the analyte and the porphyrin array, a broad spectrum of chemical species is differentiable. While long response times (e.g., about 45 minutes) are observed at low analyte concentrations of about 1 ppm with reverse phase silica gel plates, use of impermeable solid supports (such as polymer- or glass-based micro-array plates) substantially increases the low-level response to less than 5 minutes.

Thus, it is an object of the present invention to provide methods and devices for artificial olfaction, vapor-selective detectors or artificial noses for a wide variety of applications. It is another object of the present invention to provide methods of detection and artificial noses that can detect low levels of odorants and/or where odorants may be harmful to living human, animal or plant cells. It is also an object of the present invention to provide methods of olfactory detection and artificial noses that can detect and quantify many different chemicals for dosimeters that can detect chemical poisons or toxins, that can detect spoilage in foods, that can detect flavorings and additives, and that can detect plant materials, e.g., fruits and vegetables.

Another object of the present invention is to provide for the detection of analytes using data analysis/pattern recognition techniques, including automated techniques.

Another object of the invention is to provide an artificial nose comprising an array, the array comprising at least a first dye and a second dye deposited directly onto a single support in a predetermined pattern combination, the combination of the dyes in the array having a distinct and direct spectral absorbance or reflectance response to an analyte wherein the first dye and the second are selected from the group of dyes consisting of chemoresponsive dyes, and the second dye is distinct from the first dye. In one embodiment, the first dye is selected from the group consisting of porphyrin, chlorin, chlorophyll, phtahlocyanine, and salen and their metal complexes. In another embodiment, the second dye is selected from the group consisting of acid-base indicator dyes and solvatochromic dyes.

Another object of the invention is to provide a method of detecting an analyte comprising the steps of: (a) forming an array of at least a first dye and a second dye deposited directly onto a single support in a predetermined pattern combination, the combination of the dyes in the array having a distinct and direct spectral absorbance or reflectance response to an analyte wherein the first dye and the second dye are selected from the group consisting of chemoresponsive dyes, and the second dye is distinct from the first dye, (b) subjecting the array to an analyte, (c) inspecting the array for a distinct and direct spectral absorbance or reflectance response, and (d) correlating the distinct and direct spectral response to the presence of the analyte. In one embodiment, the first dye is selected from the group consisting of porphyrin, chlorin, chlorophyll, phtahlocyanine, and salen and their metal complexes. In another embodiment, the second dye is selected from the group consisting of acid-base indicator dyes and solvatochromic dyes.

Another object of the invention is to provide an artificial tongue comprising an array, the array comprising at least a first dye and a second dye deposited directly onto a single support in a predetermined pattern combination, the combination of the dyes in the array having a distinct and direct spectral absorbance or reflectance response to an analyte wherein the first dye and the second are selected from the group of dyes consisting of chemoresponsive dyes, and the second dye is distinct from the first dye. In one embodiment, the first dye is selected from the group consisting of porphyrin, chlorin, chlorophyll, phtahlocyanine, and salen and their metal complexes. In another embodiment, the second dye is selected from the group consisting of acid-base indicator dyes and solvatochromic dyes.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIGS. 14a, 14b, and 14c illustrate differences in $K_{eq}$ for various porphyrins.

DETAILED DESCRIPTION OF THE PREFERRED EMBODIMENTS

Production of the Sensor Plate of the Present Invention

Figure 1:
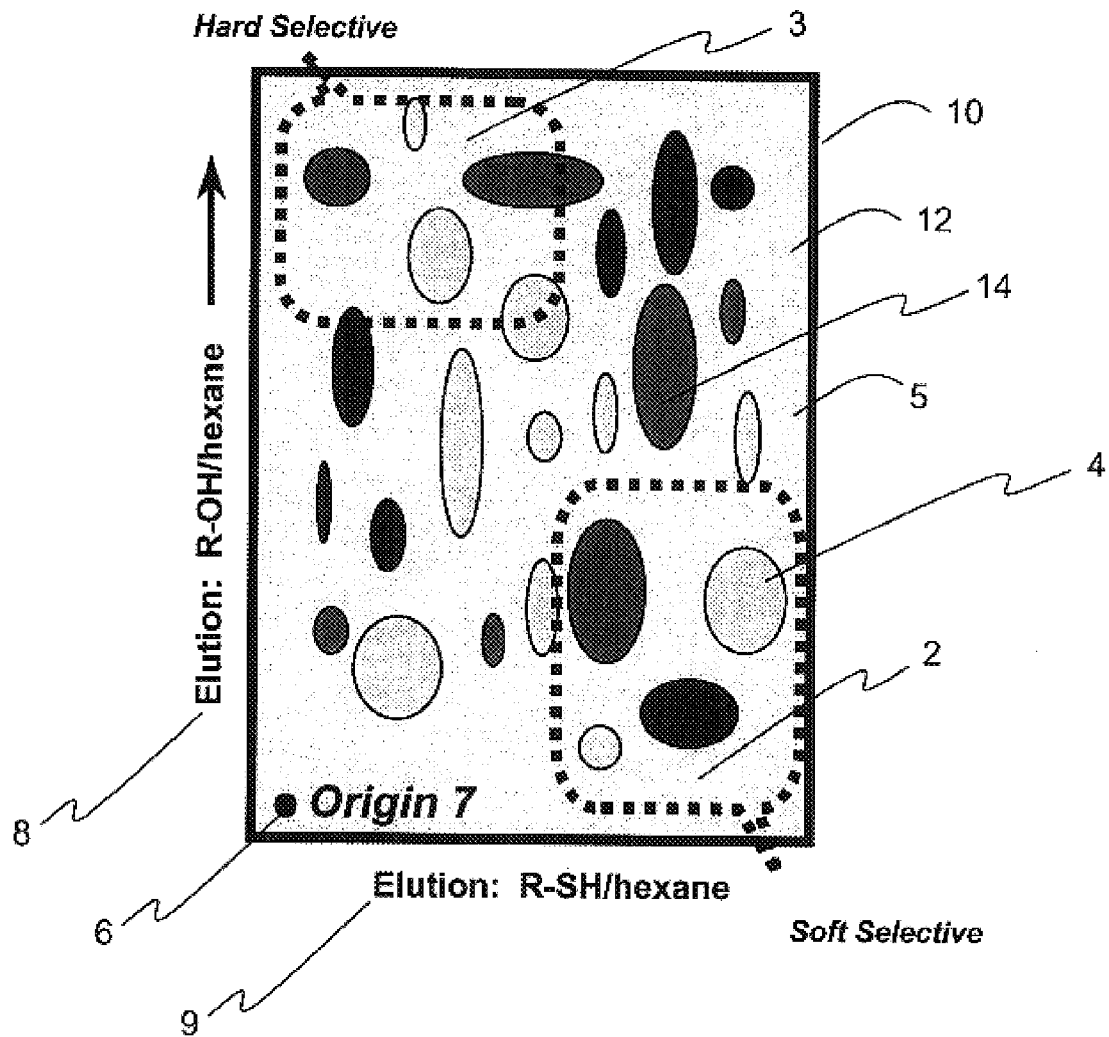
FIG. 1 illustrates an embodiment of the optical sensing plate of the present invention using a first elution in the y axis and a second elution in the x axis of the plate. In this embodiment the first elution R—OH/hexane and the second elution is R—SH/hexane.

A sensor plate 10 fabricated in accordance with the present invention is shown in FIG. 1. Sensor plate 10 comprises a two-dimensionally spatially resolved array 12 of various sensing elements or dyes 14 capable of changing color upon interaction (e.g., binding, pi-pi complexation, or polarity induced shifts in color). As shown in FIG. 1, a library of such dyes 14 can be given spatial resolution by two-dimensional chromatography or by direct deposition, including, but not limited to, ink-jet printing, micropipette spotting, screen printing, or stamping. In FIG. 1, metalloporphyrin mixture 6 is placed at origin 7. Next, the metalloporphyrin mixture 6 is eluted through a silica gel or reversed-phase silica gel 5 in sensor plate 10, and the metalloporphyrins are spatially resolved from each other and immobilized in silica gel 5 as depicted by the oval and circular shapes 4 as shown in FIG. 1. Sensor plate 10 can be made from any suitable material or materials, including but not limited to, chromatography plates, paper, filter papers, porous membranes, or properly machined polymers, glasses, or metals.

FIG. 1 also illustrates an embodiment of the optical sensing plate of the present invention using a first elution 8 in the y axis and a second elution 9 in the x axis of sensor plate 10. In this embodiment, the first elution 8 is R—OH/hexane and the second elution 9 is R—SH/hexane. The order of the first and second elutions can be reversed. The first and second elutions are used to spatially resolve the metalloporphyrin mixture 6 in silica gel 5. As shown in FIG. 1, the upper left hand quadrant 3 is characterized by metalloporphyrins that are "hard" selective, i.e., having a metal center having a high chemical hardness, i.e., a high charge density. As shown in FIG. 1, the lower right hand quadrant 2 is characterized by metalloporphyrins that are "soft" selective, i.e., having a metal center having a low chemical hardness, i.e., a low charge density. In accordance with the present invention, the array can be a spatially resolved collection of dyes, and more particularly a spatially resolved combinatorial family of dyes.

In accordance with the present invention, a porphyrin—metalloporphyrin sensor plate was prepared and then used to detect various odorants. More specifically, solutions of various metalated tetraphenylporphyrins in either methylene chloride or chlorobenzene were spotted in 1 μL aliquots onto two carbon ("C2", i.e, ethyl-capped) reverse phase silica thin layer chromatography plates (Product No. 4809-800, by Whatman, Inc., Clifton, N.J.) to yield the sensor array 16 seen in FIG. 2B. As shown in FIG. 2B and summarized in Table 1 below, the dyes have the following colors (the exact colors depend, among other things, upon scanner settings).

TABLE 1

(Summarizing Colors of Dyes in FIG. 2B)

| | | |
|---|---|---|
| $Sn^{4+}$ - Green | $Co^{3+}$ - Red | $Cr^{3+}$ - Deep Green |
| $Mn^{3+}$ - Green | $Fe^{3+}$ - Dark Red | $Co^{2+}$ - Red |
| $Cu^{2+}$ - Red | $Ru^{3+}$ - Light Yellow | $Zn^{2+}$ - Greenish Red |
| $Ag^{2+}$ - Red | $2H^{+}$ (Free Base "FB") - Red | |

Figure 2A:
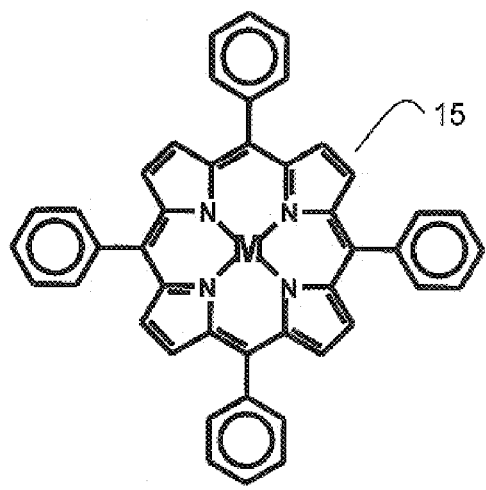
FIG. 2A illustrates an embodiment of the invention using metalloporphyrins as the sensing dyes.
Figure 2B:
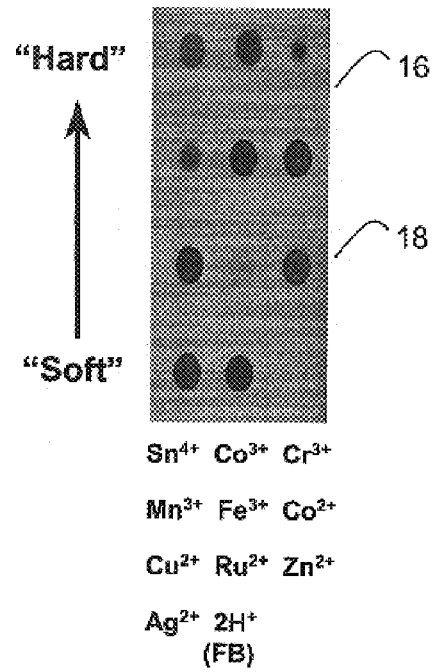
FIG. 2B illustrates an embodiment of the invention using metalloporphyrins as the sensing dyes.

A metalloporphyrin 15, sometimes referred to as M(TPP), of the present invention is depicted in FIG. 2A. FIG. 2A also depicts various metals of the metalloporphyrins 15 of the present invention, and corresponding metal ion charge to radius ratio (i.e., Z/r Ratio) in reciprocal angstroms. The Z/r Ratio should preferably span a wide range in order to target a wide range of metal ligating analytes. These metalloporphyrins have excellent chemical stability on the solid support and most have well-studied solution ligation chemistry. Reverse phase silica was chosen as a non-interacting dispersion medium for the metalloporphyrin array 16 depicted in FIG. 2B, as well as a suitable surface for diffuse reflectance spectral measurements. More importantly, the reverse phase silica presents a hydrophobic interface, which virtually eliminates interference from ambient water vapor. After spotting, sensor plates 18 like the one depicted in FIG. 2B were dried under vacuum at 50° C. for 1 hour prior to use. Thus, immobilization of the metalloporphyrins on a reverse phase silica support is obtained. While ten (10) different metalloporphyrins are shown in FIG. 2A, those of skill in the art will recognize that many other metalloporphyrins are useful in accordance with the present invention. Those of skill in the art will further recognize that in accordance with the broad teachings of the present invention, any dyes capable of changing color upon interacting with an analyte, both containing and not containing metal ions, are useful in the array of the present invention.

Colorimetric Analysis Using the Sensor Plate

For the detection and analysis of odorants in accordance with the present invention, one needs to monitor the absorbance of the sensor plate at one or more wavelengths in a spatially resolved fashion. This can be accomplished with an imaging spectrophotometer, a simple flatbed scanner (e.g. a Hewlett Packard Scanjet 3c), or an inexpensive video or CCD camera.

Figure 3A:
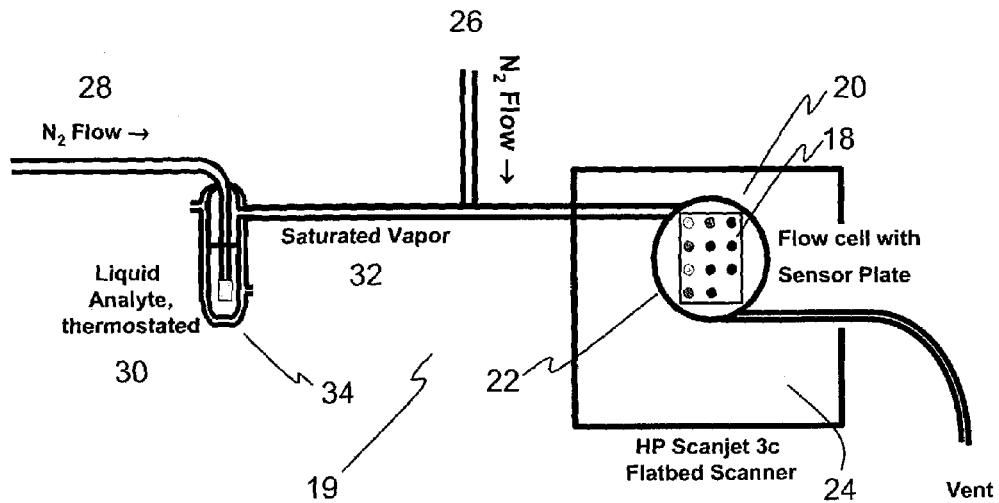
FIG. 3A illustrates a vapor exposure apparatus for demonstration of the present invention.
Figure 3B:
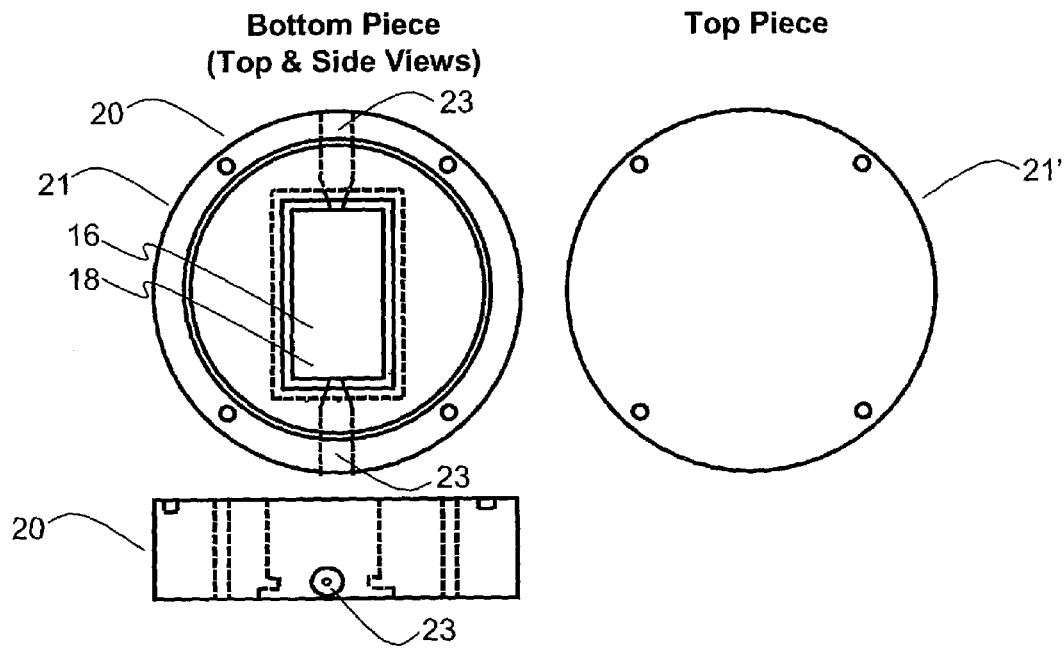
FIG. 3B illustrates a vapor exposure apparatus for demonstration of the present invention.

FIG. 3A illustrates a vapor exposure apparatus 19 of the present invention. FIG. 3B illustrates top and side views of bottom piece 21 and a top view of top piece 21' of a vapor exposure flow cell 20 of the present invention. In an embodiment of the present invention for purposes of demonstration, each sensor plate 18 was placed inside of a stainless steel flow cell 20 equipped with a quartz window 22 as shown in FIGS. 3A and 3B. Scanning of the sensor plate 18 was done on a commercially available flatbed scanner 24 (Hewlett Packard Scanjet 3c) at 200 dpi resolution, in full color mode. Following an initial scan, a control run with a first pure nitrogen flow stream 26 was performed. The array 16 of plate 18 was then exposed to a second nitrogen flow stream 28 saturated with a liquid analyte 30 of interest. As shown in FIG. 3A, the nitrogen flow stream 28 saturated with liquid analyte 30 results in a saturated vapor 32. Saturated vapor 32, containing the analyte 30 of interest were generated by flowing nitrogen flow stream 28 at 0.47 L/min. through the neat liquid analyte 30 in a water-jacketed, glass fritted bubbler 34. Vapor pressures were controlled by regulating the bubbler 34 temperature. As shown in FIG. 3B, vapor channels 23 permit vapor flow to sensor plate 18.

EXAMPLE 1

Scanning at different time intervals and subtracting the red, green and blue ("RGB") values of the new images from those of the original scan yields a color change profile. This is shown for n-butylamine in FIG. 4, in which color change profiles of the metalloporphyrin sensor array 16 as a function of exposure time to n-butylamine vapor. Subtraction of the initial scan from a scan after 5 min. of $N_2$ exposure was used as a control, giving a black response, as shown. 9.3% n-butylamine in $N_2$ was then passed over the array and scans made after exposure for 30 s, 5 min., and 15 min. The red, green and blue ("RGB") mode images were subtracted (absolute value) to produce the color change profiles illustrated. Virtually all porphyrins are saturated after 30 seconds of exposure, yielding a color fingerprint unique for each class of analytes, which is illustrated in FIG. 4.

Figure 4:
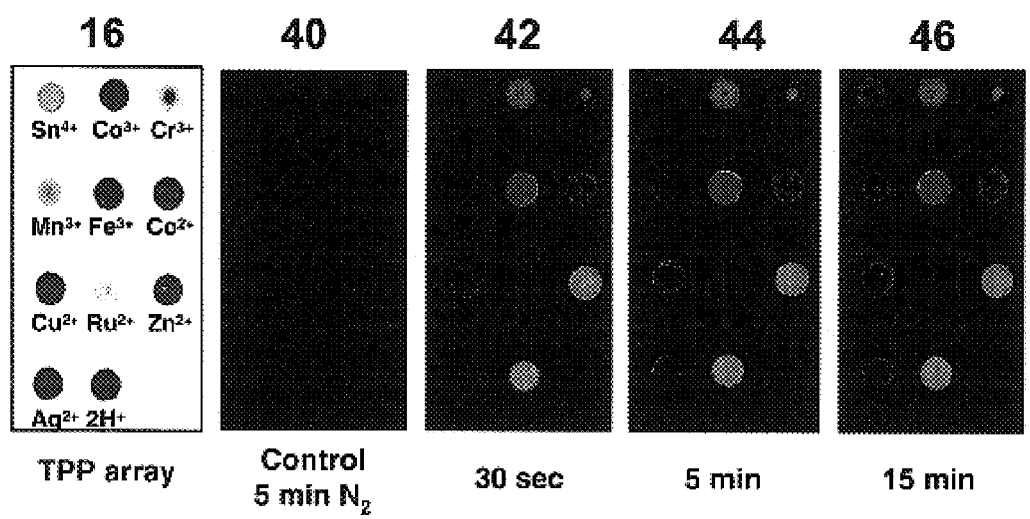
FIG. 4 illustrates the color change profile in a metalloporphyrin array of FIG. 2 when used in the vapor exposure apparatus of FIG. 3A to detect n-butylamine. Metalloporphyrins were immobilized on reverse phase silica gel plates.

More specifically, subtraction of the initial scan 40 from a scan after 5 min. of $N_2$ exposure was used as a control, giving a black response, as shown in FIG. 4. A nitrogen flow stream containing 0.093% n-butylamine was then passed over the array 16 and scans 42, 44, and 46 were made after exposure for 30 seconds, 5 minutes, and 15 minutes, respectively. The RGB mode images were subtracted (absolute value) using Adobe Photoshop™ (which comprises standard image analyzing software), with contrast enhancement by expanding the pixel range (a 32 value range was expanded to 256 each for the R, G, and B values). Subtraction of exposed and unexposed images gives color change patterns that vary in hue and intensity. Because differentiation is provided by an array of detectors, the system has parallels the mammalian olfactory system. As shown in FIG. 4 and summarized in Table 2 below, the dyes have the following colors in scans 42, 44, and 46.

TABLE 2

(Summarizing Colors of Dyes in FIG. 4, Scans 42, 44, and 46)

| | | |
|---|---|---|
| $Sn^{4+}$ - No Change | $Co^{3+}$ - Green | $Cr^{3+}$ - Green |
| $Mn^{3+}$ - No Change | $Fe^{3+}$ - Red | $Co^{2+}$ - Faint Green |
| $Cu^{2+}$ - No Change | $Ru^{2+}$ - No Change | $Zn^{2+}$ - Light Green |
| $Ag^{2+}$ - No Change | $2H^{+}$ (Free Base "FB") — Light Blue | |

As summarized in Table 3 below, for the TTP array 16 depicted on the left-hand side of FIG. 4, the dyes have the following colors.

TABLE 3

| | | |
|---|---|---|
| $Sn^{4+}$ - Greenish Yellow | $Co^{3+}$ - Red | $Cr^{3+}$ - Yellow with Dark Red Center |
| $Mn^{3+}$ - Greenish Yellow | $Fe^{3+}$ - Dark Red | $Co^{2+}$ - Red |
| $Cu^{2+}$ - Red | $Ru^{2+}$ - Light Yellow | $Zn^{2+}$ - Red |
| $Ag^{2+}$ - Red | $2H^+$ (Free Base "FB") - Red | |

EXAMPLE 2

Visible spectral shifts and absorption intensity differences occur upon ligation of the metal center, leading to readily observable color changes. As is well known to those with skill in the art, the magnitude of spectral shift correlates with the polarizability of the ligand; hence, there exists an electronic basis for analyte distinction. Using metal centers that span a range of chemical hardness and ligand binding affinity, a wide range of volatile analytes (including soft ligands, such as thiols, and harder ligands, such as amines) are differentiable. Because porphyrins have been shown to exhibit wavelength and intensity changes in their absorption bands with varying solvent polarity, it is contemplated that the methods and apparatus of the present invention can be used to calorimetrically distinguish among a series of weakly ligating solvent vapors (e.g., arenes, halocarbons, or ketones), as shown for example in FIG. 5.

Figure 5:
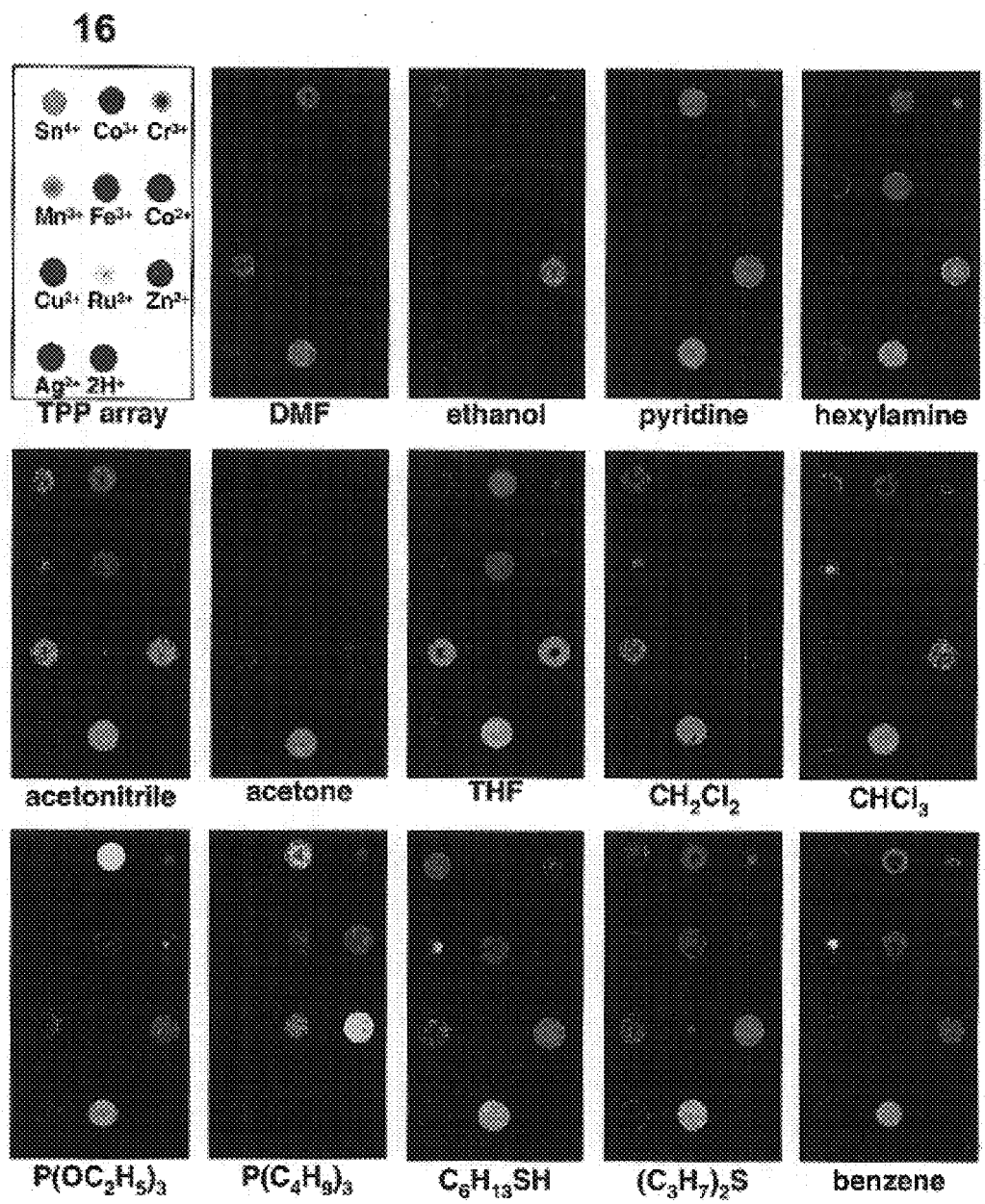
FIG. 5 illustrates a comparison of color changes at saturation for a wide range of analytes. Each analyte was delivered to the array as a nitrogen stream saturated with the analyte vapor at 20° C. DMF stands for dimethylformamide; THF stands for tetrahydrofuran.

A comparison of color changes at saturation for a wide range of analytes is shown in FIG. 5. Each analyte is identified under the colored array 16 that identifies each analyte.). DMF stands for the analyte dimethylformamide, and THF stands for the analyte tetrahydrofuran. As shown in FIG. 5 and summarized in Table 4 below, the colors of each dye in response to a particular analyte are as follows.

TABLE 4

Analyte: DMF

| | | |
|---|---|---|
| $Sn^{4+}$ - No Change | $Co^{3+}$ - Green | $Cr^{3+}$ - No Change |
| $Mn^{3+}$ - No Change | $Fe^{3+}$ - No Change | $Co^{2+}$ - No Change |
| $Cu^{2+}$ - Blue | $Ru^{2+}$ - No Change | $Zn^{2+}$ - No Change |
| $Ag^{2+}$ - No Change | $2H^+$ (Free Base "FB") - Blue | |

Analyte: Ethanol

| | | |
|---|---|---|
| $Sn^{4+}$ - Dark Blue | $Co^{3+}$ - No Change | $Cr^{3+}$ - Red |
| $Mn^{3+}$ - No Change | $Fe^{3+}$ - No Change | $Co^{2+}$ - No Change |
| $Cu^{2+}$ - No Change | $Ru^{2+}$ - No Change | $Zn^{2+}$ - Blue |
| $Ag^{2+}$ - No Change | $2H^+$ (Free Base "FB") - No Change | |

Analyte: Pyridine

| | | |
|---|---|---|
| $Sn^{4+}$ - No Change | $Co^{3+}$ - Green | $Cr^{3+}$ - Dark Green |
| $Mn^{3+}$ - No Change | $Fe^{3+}$ - No Change | $Co^{2+}$ - No Change |
| $Cu^{2+}$ - No Change | $Ru^{2+}$ - No Change | $Zn^{2+}$ - Green |
| $Ag^{2+}$ - No Change | $2H^+$ (Free Base "FB") - Blue | |

Analyte: Hexylamine

| | | |
|---|---|---|
| $Sn^{4+}$ - No Change | $Co^{3+}$ - Dark Green | $Cr^{3+}$ - Green |
| $Mn^{3+}$ - No Change | $Fe^{3+}$ - Red | $Co^{2+}$ - No Change |
| $Cu^{2+}$ - Blue | $Ru^{2+}$ - No Change | $Zn^{2+}$ - Green |
| $Ag^{2+}$ - Dark Blue | $2H^+$ (Free Base "FB") - Blue | |

Analyte: Acetonitrile

| | | |
|---|---|---|
| $Sn^{4+}$ - Blue | $Co^{3+}$ - Dark Green | $Cr^{3+}$ - No Change |
| $Mn^{3+}$ - Yellow | $Fe^{3+}$ - Dark Green | $Co^{2+}$ - No Change |
| $Cu^{2+}$ - Blue | $Ru^{2+}$ - Blue (faint dot) | $Zn^{2+}$ - Blue |
| $Ag^{2+}$ - No Change | $2H^+$ (Free Base "FB") - Blue | |

Analyte: Acetone

| | | |
|---|---|---|
| $Sn^{4+}$ - No Change | $Co^{3+}$ - No Change | $Cr^{3+}$ - Red (small dot) |
| $Mn^{3+}$ - No Change | $Fe^{3+}$ - No Change | $Co^{2+}$ - No Change |
| $Cu^{2+}$ - Dark Blue | $Ru^{2+}$ - No Change | $Zn^{2+}$ - Dark Blue |
| $Ag^{2+}$ - No Change | $2H^+$ (Free Base "FB") - Blue | |

Analyte: THF

| | | |
|---|---|---|
| $Sn^{4+}$ - Dark Blue | $Co^{3+}$ - Green | $Cr^{3+}$ - Red |
| $Mn^{3+}$ - Blue (small dot) | $Fe^{3+}$ - Dark Green | $Co^{2+}$ - No Change |
| $Cu^{2+}$ - Blue | $Ru^{2+}$ - No Change | $Zn^{2+}$ - Blue |
| $Ag^{2+}$ - No Change | $2H^+$ (Free Base "FB") - Blue | |

Analyte: $CH_2Cl_2$

| | | |
|---|---|---|
| $Sn^{4+}$ - Dark Blue | $Co^{3+}$ - No Change | $Cr^{3+}$ - No Change |
| $Mn^{3+}$ - Yellow and Red (small dot) | $Fe^{3+}$ - No Change | $Co^{2+}$ - No Change |
| $Cu^{2+}$ - Dark Blue | $Ru^{2+}$ - No Change | $Zn^{2+}$ - No Change |
| $Ag^{2+}$ - No Change | $2H^+$ (Free Base "FB") - Blue | |

TABLE 4-continued

Analyte: CHCl₃

| | | |
|---|---|---|
| $Sn^{4+}$ - Dark Blue | $Co^{3+}$ - Dark Green | $Cr^{3+}$ - Yellow (circle) |
| $Mn^{3+}$ - Yellow | $Fe^{3+}$ - Dark Green (very faint) | $Co^{2+}$ - No Change |
| $Cu^{2+}$ - Dark Blue (very faint) | $Ru^{2+}$ - No Change | $Zn^{2+}$ - Blue |
| $Ag^{2+}$ - Blue (very faint) | $2H^+$ (Free Base "FB") - Blue | |

Analyte: $P(OC_2H_5)_3$

| | | |
|---|---|---|
| $Sn^{4+}$ - No Change | $Co^{3+}$ - Yellow | $Cr^{3+}$ - Dark Green |
| $Mn^{3+}$ - No Change | $Fe^{3+}$ - Dark Green (very faint) | $Co^{2+}$ - Greenish Yellow |
| $Cu^{2+}$ - Dark Blue (faint) | $Ru^{2+}$ - No Change | $Zn^{2+}$ - Greenish Blue |
| $Ag^{2+}$ - Blue (very faint) | $2H^+$ (Free Base "FB") - Blue | |

Analyte: $P(C_4H_9)_3$

| | | |
|---|---|---|
| $Sn^{4+}$ - No Change | $Co^{3+}$ - Yellow and Red | $Cr^{3+}$ - Deep Red |
| $Mn^{3+}$ - No Change | $Fe^{3+}$ - Dark Green (faint) | $Co^{2+}$ - Red (with some yellow) |
| $Cu^{2+}$ - No Change | $Ru^{2+}$ - Dark Blue | $Zn^{2+}$ - Yellow |
| $Ag^{2+}$ - No Change | $2H^+$ (Free Base "FB") - No Change | |

Analyte: $C_6H_{13}SH$

| | | |
|---|---|---|
| $Sn^{4+}$ - Green | $Co^{3+}$ - No Change | $Cr^{3+}$ - Yellow circle surrounded by greenish blue circle |
| $Mn^{3+}$ - Yellow | $Fe^{3+}$ - Dark Green | $Co^{2+}$ - No Change |
| $Cu^{2+}$ - Dark Blue (faint) | $Ru^{2+}$ - No Change | $Zn^{2+}$ - Green |
| $Ag^{2+}$ - Blue (very faint) | $2H^+$ (Free Base "FB") - Blue | |

Analyte: $(C_3H_7)_2S$

| | | |
|---|---|---|
| $Sn^{4+}$ - Dark Blue (faint) | $Co^{3+}$ - Deep Green | $Cr^{3+}$ - Green |
| $Mn^{3+}$ - No Change | $Fe^{3+}$ - Dark Green | $Co^{2+}$ - Dark Green (very faint) |
| $Cu^{2+}$ - Dark Blue (faint) | $Ru^{2+}$ - Green | $Zn^{2+}$ - Green |
| $Ag^{2+}$ - Blue (very faint) | $2H^+$ (Free Base "FB") - Blue | |

Analyte: Benzene

| | | |
|---|---|---|
| $Sn^{4+}$ - No Change | $Co^{3+}$ - Green | $Cr^{3+}$ - Yellow (very faint) |
| $Mn^{3+}$ - Yellow (some green) | $Fe^{3+}$ - Dark Green | $Co^{2+}$ - No Change |
| $Cu^{2+}$ - No Change | $Ru^{2+}$ - No Change | $Zn^{2+}$ - Dark Green |
| $Ag^{2+}$ - No Change | $2H^+$ (Free Base "FB") - Blue | |

The degree of ligand softness (roughly their polarizability) increases from left to right, top to bottom as shown in FIG. 1. Each analyte is easily distinguished from the others, and there are family resemblances among chemically similar species (e.g., pyridine and n-hexylamine). Analyte distinction originates both in the metal-specific ligation affinities and in their specific, unique color changes upon ligation. Each analyte was delivered to the array as a nitrogen stream saturated with the analyte vapor at 20° C. (to ensure complete saturation, 30 min. exposures to vapor were used. Although these fingerprints were obtained by exposure to saturated vapors (thousands of ppm), unique patterns can be identified at much lower concentrations.

The metalloporphyrin array 16 has been used to quantify single analytes and to identify vapor mixtures. Because the images' color channel data (i.e., RGB values) vary linearly with porphyrin concentration, we were able to quantify single porphyrin responses to different analytes. Color channel data were collected for individual spots and plotted, for example, as the quantity $(R_{plt}-R_{spt})/(R_{plt})$, where $R_{plt}$ was the red channel value for the initial silica surface and $R_{spt}$ the average value for the spot. For example, Fe(TFPP)(Cl) responded linearly to octylamine between 0 and 1.5 ppm. Other porphyrins showed linear response ranges that varied with ligand affinity (i.e., equilibrium constant).

EXAMPLE 3

Figure 6:
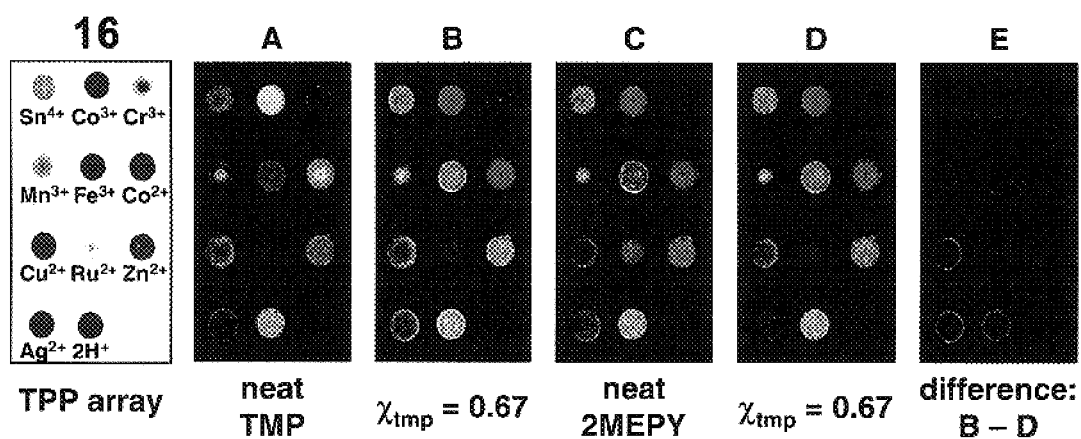
FIG. 6 illustrates two component saturation responses of mixtures of 2-methylpyridine and trimethylphosphite. Vapor mixtures were obtained by mixing two analyte-saturated $N_2$ streams at variable flow ratios.

The array of the present invention has demonstrated interpretable and reversible responses even to analyte mixtures of strong ligands, such as pyridines and phosphites, as is shown in FIG. 6. Color change patterns for the mixtures are distinct from either of the neat vapors. Good reversibility was demonstrated for this analyte pair as the vapor mixtures were cycled between the neat analyte extremes, as shown in FIG. 6, which shows the two component saturation responses to mixtures of 2-methylpyridine ("2MEPY") and trimethylphosphite ("TMP"). Vapor mixtures were obtained by mixing the analyte-saturated $N_2$ streams at variable flow ratios. A single plate was first exposed to pure trimethylphosphite vapor in $N_2$ (Scan A), followed by increasing mole fractions of 2-methylpyridine up to pure 2-methylpyridine vapor (Scan C), followed by decreasing mole fractions of 2-methylpyridine back to pure trimethylphosphite vapor. In both directions, scans were taken at the same mole fraction trimethylphosphite and showed excellent reversibility; scans at mole fractions at 67% trimethylphosphite ($\chi_{tmp}=0.67$, Scans B and D) and of their difference map are shown (Scan E). Response curves for the individual porphyrins allow for quantification of the mixture composition. The colors of each dye upon exposure to the analytes TMP and 2MEPY are shown in FIG. 6 and are summarized in Table 5 below.

TABLE 5

Scan A, Analyte: Neat TMP

| | | |
|---|---|---|
| $Sn^{4+}$ - Dark Blue | $Co^{3+}$ - Yellow | $Cr^{3+}$ - No Change |
| $Mn^{3+}$ - Yellow with red center | $Fe^{3+}$ - Dark Green | $Co^{2+}$ - Greenish Yellow |
| $Cu^{2+}$ - Dark Blue | $Ru^{2+}$ - No Change | $Zn^{2+}$ - Blue |
| $Ag^{2+}$ - Green (very faint) | $2H^+$ (Free Base "FB") — Reddish Blue | |

Scan B, Analyte: TMP, $x_{TMP} = 0.67$

| | | |
|---|---|---|
| $Sn^{4+}$ - Blue | $Co^{3+}$ - Green | $Cr^{3+}$ - Green (small dot) |
| $Mn^{3+}$ - Yellow and Green | $Fe^{3+}$ - Green and Yellow | $Co^{2+}$ - Green with red center |
| $Cu^{2+}$ - Dark Blue | $Ru^{2+}$ - Purple (very faint) | $Zn^{2+}$ - Blue |
| $Ag^{2+}$ - Greenish Blue | $2H^+$ (Free Base "FB") — Reddish Blue | |

Scan C, Analyte: Neat 2MEPY

| | | |
|---|---|---|
| $Sn^{4+}$ - Blue | $Co^{3+}$ - Green | $Cr^{3+}$ - No Change |
| $Mn^{3+}$ - Yellow and Green with Red center | $Fe^{3+}$ - Red with some Yellow | $Co^{2+}$ - Green |
| $Cu^{2+}$ - Dark Blue | $Ru^{2+}$ - Deep Blue | $Zn^{2+}$ - Green with some Blue |
| $Ag^{2+}$ - Green with some Blue | $2H^+$ (Free Base "FB") — Reddish Blue | |

Scan D, Analyte: TMP, $x_{TMP} = 0.67$

| | | |
|---|---|---|
| $Sn^{4+}$ - Blue | $Co^{3+}$ - Green | $Cr^{3+}$ - No Change |
| $Mn^{3+}$ - Yellow and Green | $Fe^{3+}$ - Green and Yellow | $Co^{2+}$ - Green |
| $Cu^{2+}$ - Dark Blue | $Ru^{2+}$ - Purple (very faint) | $Zn^{2+}$ - Blue |
| $Ag^{2+}$ - Greenish Blue (very faint) | $2H^+$ (Free Base "FB") — Reddish Blue | |

Scan E

| | | |
|---|---|---|
| $Sn^{4+}$ - No Change | $Co^{3+}$ - No Change | $Cr^{3+}$ - No Change |
| $Mn^{3+}$ - No Change | $Fe^{3+}$ - No Change | $Co^{2+}$ - No Change |
| $Cu^{2+}$ - Blue (very faint) | $Ru^{2+}$ - Blue (small dot) | $Zn^{2+}$ - No Change |
| $Ag^{2+}$ - Blue (very faint) | $2H^+$ (Free Base "FB") - Green | |

EXAMPLE 4

Figure 7:
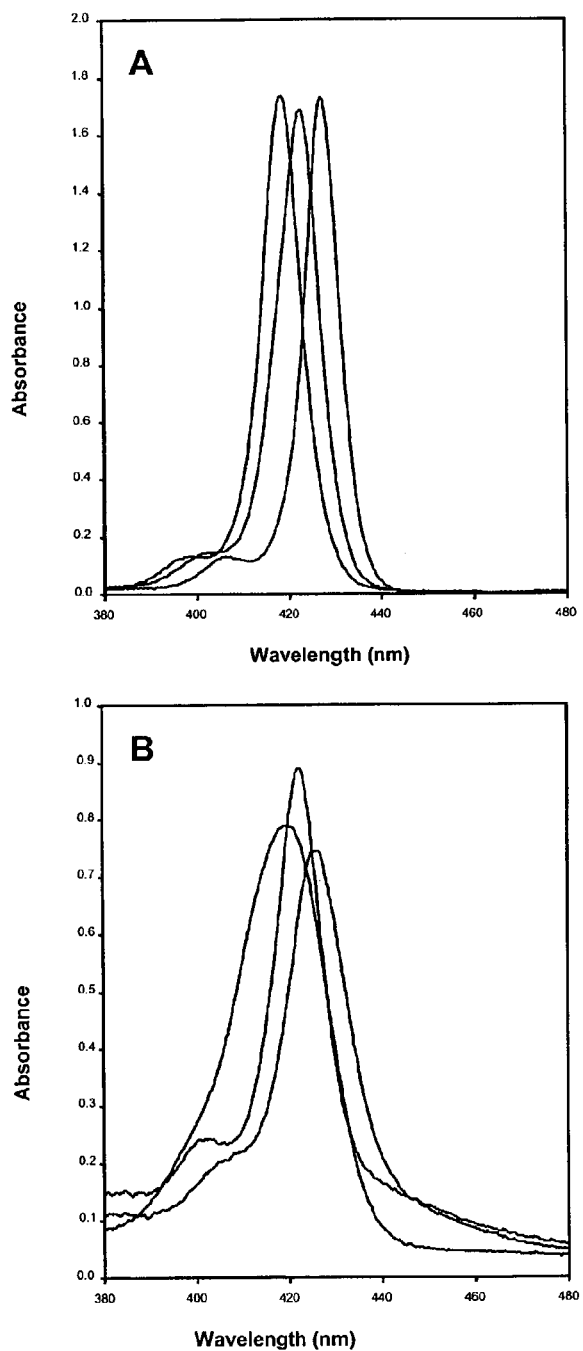
FIG. 7 illustrates a comparison of Zn(TPP) spectral shifts upon exposure to ethanol and pyridine (py) in methylene chloride solution (A) and on the reverse phase support (B).

In an effort to understand the origin of the color changes upon vapor exposure, diffuse reflectance spectra were obtained for single porphyrin spots before and after exposure to analyte vapors. Porphyrin solutions were spotted in 50 μL aliquots onto a plate and allowed to dry under vacuum at 50° C. Diffuse reflectance spectra of the plate were then taken using a UV-visible spectrophotometer equipped with an integrating sphere. Unique spectral shifts were observed upon analyte exposure, which correlated well with those seen from solution ligation. For example, Zn(TPP) exposure to ethanol and pyridine gave unique shifts which were very similar to those resulting from ligand exposure in solution. FIG. 7 shows a comparison of Zn(TPP) spectral shifts upon exposure to ethanol and pyridine (py) in methylene chloride solution (A) and on the reverse phase support (B). In both A and B, the bands correspond, from left to right, to Zn(TPP), Zn(TPP)($C_2H_5OH$), and Zn(TPP)(py), respectively. Solution spectra (A) were collected using a Hitachi U-3300 spectrophotometer; Zn(TPP), $C_2H_5OH$, and py concentrations were approximately 2 μM, 170 mM, and 200 μM, respectively. Diffuse reflectance spectra (B) were obtained with an integrating sphere attachment before exposure to analytes, after exposure to ethanol vapor in $N_2$, and after exposure to pyridine vapor in $N_2$ for 30 min. each using the flow cell.

Improvement to Low Concentration Response

Color changes at levels as low as 460 ppb have been observed for octylamine vapor, albeit with slow response times due to the high surface area of the silica on the plate 18. The surface area of C2 plates is ≈350 $m^2$/gram. Removal of excess silica gel surrounding the porphyrin spots from the plate 18 led to substantial improvements in response time for exposures to trace levels of octylamine. Because the high surface area of the reverse phase silica surface is primarily responsible for the increased response time, other means of solid support or film formation can be used to improve low concentration response.

Further, the present invention contemplates miniaturization of the array using small wells 60 (<1 mm), for example in glass, quartz, or polymers, to hold metalloporphyrin or other dyes as thin films, which are deposited as a solution, by liquid droplet dispersion (e.g., airbrush or inkjet), or deposited as a solution of polymer with metalloporphyrin.

Figure 8:
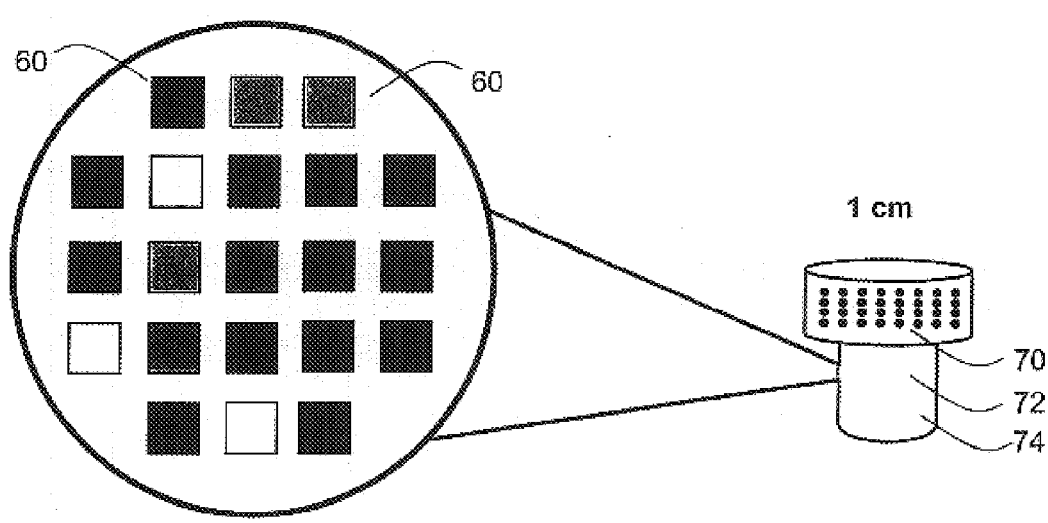
FIG. 8 illustrates another embodiment of the present invention, and more particularly, an small array comprising microwells built into a wearable detector which also contains a portable light source and a light detector, such as a charge-coupled device (CCD) or photodiode array.
Figure 9:
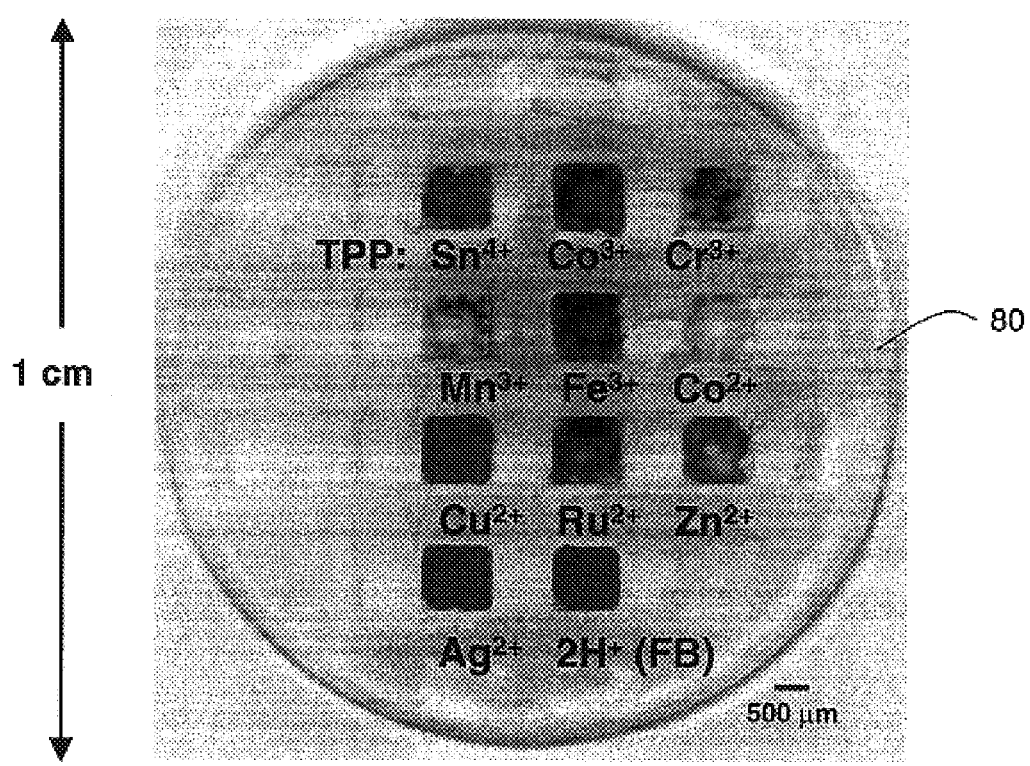
FIG. 9 illustrates another embodiment of the present invention, and more particularly, a microwell porphyrin array wellplate constructed from polydimethylsiloxane (PDMS).
Figure 10:
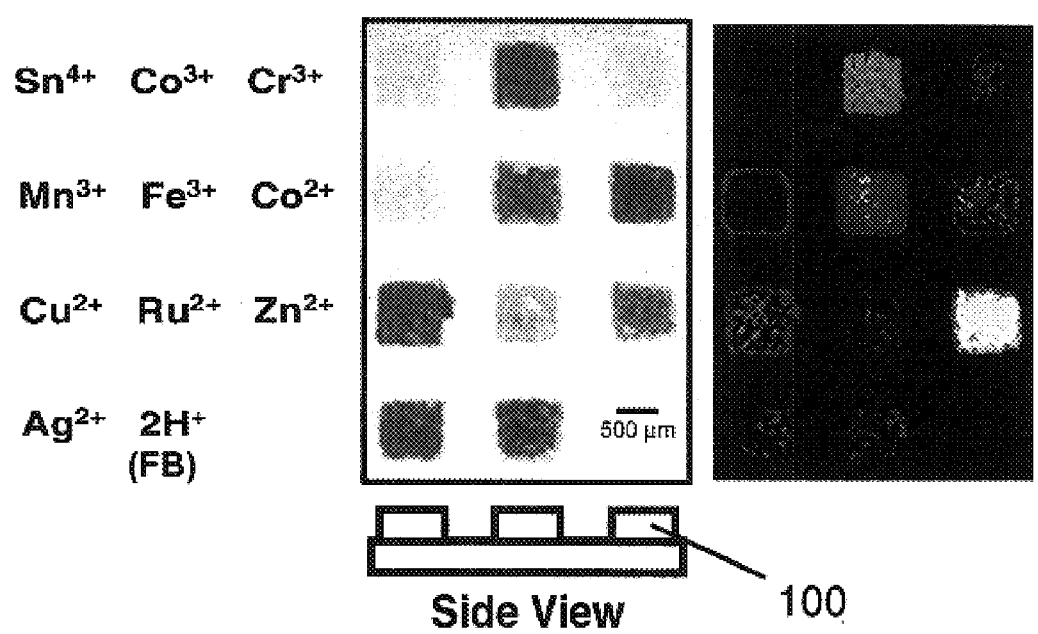
FIG. 10 illustrates another embodiment of the present invention, and more particularly, a microplate containing machined teflon posts, upon which the porphyrin array is immobilized in a polymer matrix (polystyrene/dibutylphthalate).

These embodiments are depicted in FIGS. 8, 9, and 10. FIG. 8 illustrates the interfacing of a microplate 60 into an assembly consisting of a CCD 70, a microplate 72 and a light source 74. FIG. 9 illustrates another embodiment of the present invention, and more particularly, a microwell porphyrin array wellplate 80 constructed from polydimethylsiloxane (PDMS). The colors of the dyes shown in FIG. 9 are summarized below in Table 6.

TABLE 6

| | | |
|---|---|---|
| $Sn^{4+}$ - Dark Red | $Co^{3+}$ - Dark Red | $Cr^{3+}$ - Dark Green |
| $Mn^{3+}$ - Green | $Fe^{3+}$ - Dark Red | $Co^{2+}$ - Yellowish Green |
| $Cu^{2+}$ - Deep Red | $Ru^{2+}$ - Dark Red | $Zn^{2+}$ - Red with some Yellow |
| $Ag^{2+}$ - Red | $2H^+$ (Free Base "FB") — Red | |

FIG. 10 demonstrates deposition of metalloporphyrin/polymer (polystyrene/dibutylphthalate) solutions upon a plate, which includes a series of micro-machined Teflon® posts 100 having the same basic position relative to each other as shown in FIG. 2A and FIG. 2B. The colors for the dyes in the middle of FIG. 10 are summarized in Table 7 below.

TABLE 7

| | | |
|---|---|---|
| $Sn^{4+}$ - Yellow | $Co^{3+}$ - Orange | $Cr^{3+}$ - Yellow |
| $Mn^{3+}$ - Yellow | $Fe^{3+}$ - Orange | $Co^{2+}$ - Orange |
| $Cu^{2+}$ - Orange | $Ru^{2+}$ - Dark Yellow | $Zn^{2+}$ - Orange |
| $Ag^{2+}$ - Orange | $2H^+$ (Free Base "FB") - Red | |

The colors for the dyes on the right hand side of FIG. 10 are summarized in Table 8 below.

TABLE 8

| | | |
|---|---|---|
| $Sn^{4+}$ - No Change | $Co^{3+}$ - Green | $Cr^{3+}$ - Red |
| $Mn^{3+}$ - Blue | $Fe^{3+}$ - Red | $Co^{2+}$ - Red, Green, Blue, and Yellow |
| $Cu^{2+}$ - Green with some Blue | $Ru^{2+}$ - Blue (very faint) | $Zn^{2+}$ - Yellow with some Red |
| $Ag^{2+}$ - Green with some Blue | $2H^+$ (Free Base "FB") - Green with some Blue | |

EXAMPLE 5

Figure 11:
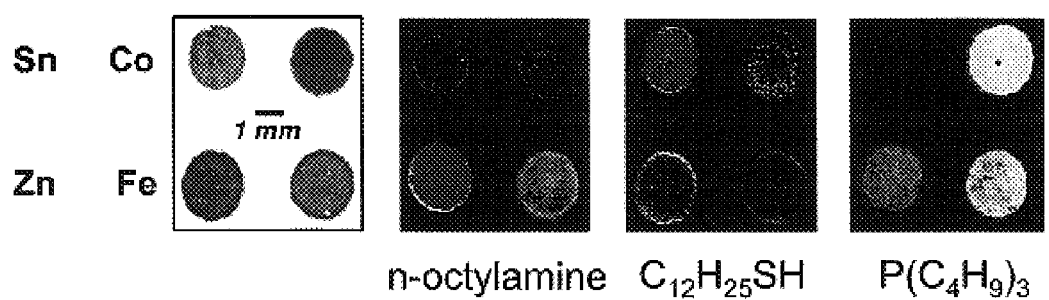
FIG. 11 illustrates another embodiment of the present invention, showing a microplate of the type shown in FIG. 10, consisting of a minimized array of four metalloporphyrins, showing the color profile changes for n-octylamine, dodecanethiol, and tri-n-butylphosphine, each at 1.8 ppm.

FIG. 11 shows the color profile changes from a microplate of the type shown in FIG. 10. The microplate, consisting of a minimized array of four metalloporphyrins, i.e., Sn(TPP)(Cl$_2$), Co(TPP)(Cl), Zn(TPP), Fe(TFPP)(Cl), clockwise from the upper left (where TFPP stands for 5,10,15,20-tetrakis(pentafluorophenyl)porphyrinate). The color profile changes are shown in FIG. 11 after exposure to low levels of n-octylamine, dodecanethiol ($C_{12}H_{25}$ SH), and tri-n-butylphosphine ($P(C_4H_9)_3$), each at 1.8 ppm, which is summarized in Table 9 below.

The low ppm levels of octylamine, an analyte of interest, were generated from temperature-regulated octylamine/dodecane solutions with the assumption of solution ideality. The dodecane acts as a diluent to lower the level of octylamine vapor pressure for the purposes of this demonstration of the invention.

EXAMPLE 6

Figure 12:
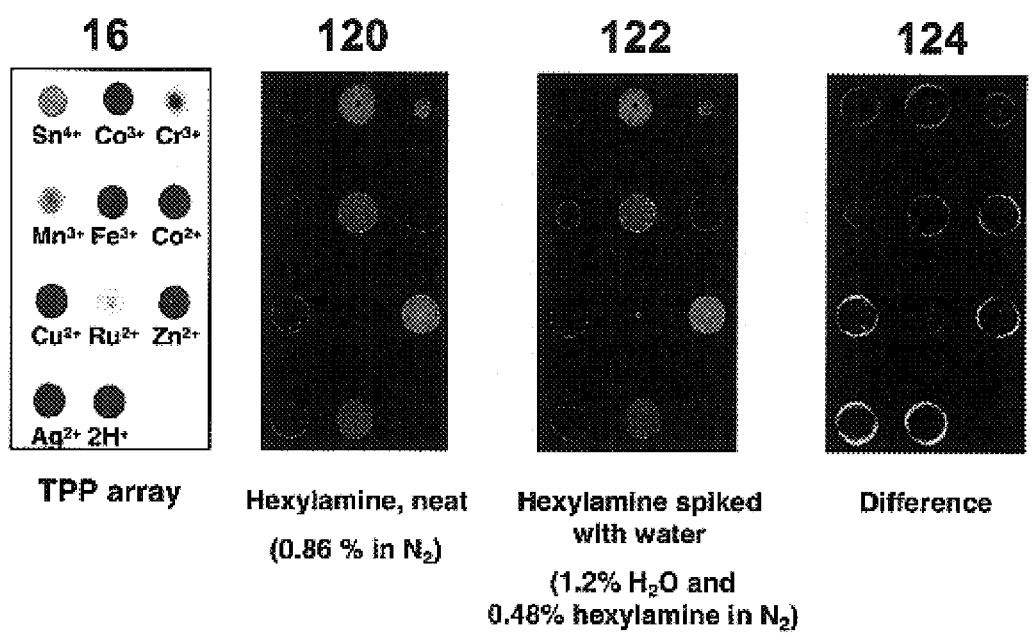
FIG. 12 illustrates the immunity of the present invention to interference from water vapor.

FIG. 12 illustrates the immunity of the present invention to interference from water vapor. The hydrophobicity of the reverse phase support greatly any possible effects from varying water vapor in the atmosphere to be tested. For instance, as shown in FIG. 12, a color fingerprint generated from exposure of the array to n-hexylamine (0.86% in N$_2$) was identical to that for n-hexylamine spiked heavily with water vapor (1.2% H$_2$O, 0.48% hexylamine in N$_2$). See scans 120, 122 and 124. The ability to easily detect species in the presence of a large water background represents a substantial advantage over mass-sensitive sensing techniques or methodologies that employ polar polymers as part of the sensor array. The color patterns shown in FIG. 12 are summarized in Table 10 below.

TABLE 9

| Dyes on Teflon ® | |
|---|---|
| Sn - Dark Yellow | Co - Red |
| Zn - Red | Fe - Orange with Red outline |
| Dyes exposed to n-octylamine | |
| Sn - No Change | Co - Green (very faint) |
| Zn - Red | Fe - Green |
| Dyes exposed to $C_{12}H_{25}SH$ | |
| Sn - Red | Co - Green with some red, yellow and blue (faint) |
| Zn - Red with some green and yellow | Fe - Blue (very faint) |
| Dyes exposed to $P(C_4H_9)_3$ | |
| Sn - No Change | Co - Yellow with red center and some red periphery |
| Zn - Green | Fe - Yellow with some Green and Blue |

TABLE 10

Scan 120

| | | |
|---|---|---|
| $Sn^{4+}$ - No Change | $Co^{3+}$ - Green | $Cr^{3+}$ - Green |
| $Mn^{3+}$ - No Change | $Fe^{3+}$ - Red | $Co^{2+}$ - No Change |
| $Cu^{2+}$ - No Change | $Ru^{2+}$ - No Change | $Zn^{2+}$ - Green |
| $Ag^{2+}$ - No Change | $2H^+$ (Free Base "FB") - Dark Blue | |

Scan 122

| | | |
|---|---|---|
| $Sn^{4+}$ - No Change | $Co^{3+}$ - Green | $Cr^{3+}$ - Green |
| $Mn^{3+}$ - No Change | $Fe^{3+}$ - Red | $Co^{2+}$ - No Change |
| $Cu^{2+}$ - No Change | $Ru^{2+}$ - Green (small dot) | $Zn^{2+}$ - Green |
| $Ag^{2+}$ - No Change | $2H^+$ (Free Base "FB") - Dark Blue | |

Scan 124

| | | |
|---|---|---|
| $Sn^{4+}$ - Bluish Circle | $Co^{3+}$ - Bluish Circle | $Cr^{3+}$ - Bluish Circle |
| $Mn^{3+}$ - Bluish Circle | $Fe^{3+}$ - Bluish Circle | $Co^{2+}$ - Bluish Circle |
| $Cu^{2+}$ - Bluish Circle | $Ru^{2+}$ - Bluish Circle | $Zn^{2+}$ - Bluish Circle |
| $Ag^{2+}$ - Bluish Circle | $2H^+$ (Free Base "FB") - Bluish Circle | |

Additional Features of the Preferred Embodiments of the Invention

Having demonstrated electronic differentiation, an important further goal is the shape-selective distinction of analytes (e.g., n-hexylamine vs. cyclohexylamine). Functionalized metalloporphyrins that limit steric access to the metal ion are candidates for such differentiation. For instance, we have been able to control ligation of various nitrogenous ligands to dendrimer-metalloporphyrins and induce selectivities over a range of more than $10^4$. As an initial attempt toward shape-selective detection, we employed the slightly-hindered tetrakis(2,4,6-trimethoxyphenyl)porphyrins (TTMPP) in our sensing array. With these porphyrins, fingerprints for t-butylamine and n-butylamine showed subtle distinctions, as did those for cyclohexylamine and n-hexylamine. Using more hindered metalloporphyrins, it is contemplated that the present invention can provide greater visual differentiation. Such porphyrins include those whose periphery is decorated with dendrimer, siloxyl, phenyl, t-butyl and other bulky substituents, providing sterically constrained pockets on at least one face (and preferably both) of the porphyrin.

In a similar fashion, it is contemplated that the sensor plates of the present invention can be used for the detection of analytes in liquids or solutions, or solids. A device that detects an analyte in a liquid or solution or solid can be referred to as an artificial tongue. Proper choice of the metal complexes and the solid support must preclude their dissolution into the solution to be analyzed. It is preferred that the surface support repel any carrier solvent to promote the detection of trace analytes in solution; for example, for analysis of aqueous solutions, reverse phase silica has advantages as a support since it will not be wetted directly by water.

Alternative sensors in accordance with the present invention may include any other dyes or metal complexes with intense absorbance in the ultraviolet, visible, or near infrared spectra that show a color change upon exposure to analytes. These alternative sensors include, but are not limited to, a variety of macrocycles and non-macrocycles such as chlorins and chlorophylls, phthalocyanines and metallophthalocyanines, salen-type compounds and their metal complexes, or other metal-containing dyes.

The present invention can be used to detect a wide variety of analytes regardless of physical form of the analytes. That is, the present invention can be used to detect any vapor emitting substance, including liquid, solid, or gaseous forms, and even when mixed with other vapor emitting substances, such solution mixtures of substances.

The present invention can be used in combinatorial libraries of metalloporphyrins for shape selective detection of substrates where the substituents on the periphery of the macrocycle or the metal bound by the porphyrin are created and then physically dispersed in two dimensions by (partial) chromatographic or electrophoretic separation.

The present invention can be used with chiral substituents on the periphery of the macrocycle for identification of chiral substrates, including but not limited to drugs, natural products, blood or bodily fluid components.

The present invention can be used for analysis of biological entities based on the surface proteins, oligosacharides, antigens, etc., that interact with the metalloporphyrin array sensors of the present invention. Further, the sensors of the present invention can be used for specific recognition of individual species of bacteria or viruses.

The present invention can be used for analysis of nucleic acid sequences based on sequence specific the surface interactions with the metalloporphyrin array sensors. The sensors of the present invention can be used for specific recognition of individual sequences of nucleic acids. Substituents on the porphyrins that would be particularly useful in this regard are known DNA intercalating molecules and nucleic acid oligomers.

The present invention can be used with ordinary flat bed scanners, as well as portable miniaturized detectors, such as CCD detectors with microarrays of dyes such as metalloporphyrins.

The present invention can be used for improved sensitivity, automation of pattern recognition of liquids and solutions, and analysis of biological and biochemical samples.

Superstructure Bonded to the Periphery of the Porphyrin

The present invention includes modified porphyrins that have a super structure bonded to the periphery of the porphyrin. A super structure bonded to the periphery of the porphyrin in accordance with the present invention includes any additional structural element or chemical structure built at the edge of the porphyrin and bonded thereto.

The super structures can include any structural element or chemical structure characterized in having a certain selectivity. Those of skill in the art will recognize that the super structures of the present invention include structures that are shape selective, polarity selective, inantio selective, regio selective, hydrogen bonding selective, and acid-base selective. This structures can include siloxyl-substituted substituents, nonsiloxyl-substituted substituents and nonsiloxyl-substituted substituents, including but not limited to aryl substituents, alkyl substituents, and organic, organometallic, and inorganic functional group substituents.

Superstructure Bis-Pocket Porphyrins

A number of modified porphyrins have been synthesized to mimic various aspects of the enzymatic functions of heme proteins, especially oxygen binding (myoglobin and hemoglobin) and substrate oxidation (cytochrome P-450). See Suslick, K. S.; Reinert, T. J. J. Chem. Ed. 1985, 62, 974; Collman, J. P.; Zhang, X.; Lee, V. J.; Uffelman, E. S.; Brauman, J. I. Science 1993,261, 1404; Collman, J. P.; Zhang, X. in Comprehensive Supramolecular Chemistry; Atwood, J. L.; Davies, J. E. D.; MacNicol, D. D.; Vogtel, F. Eds.; Pergamon: New York, 1996; vol. 5, pp. 1-32; Suslick, K. S.; van Deusen-Jeffries, S. in Comprehensive Supramolecular Chemistry; Atwood, J. L.; Davies, J. E. D.; MacNicol, D. D.; Vogtel, F. Eds.; Pergamon: New York, 1996; vol. 5, pp. 141-170; Suslick, K. S. in Activation and Functionalization of Alkanes; Hill, C. L., ed.; Wiley & Sons: New York, 1989; pp. 219-241. The notable property of many heme proteins is their remarkable substrate selectivity; the development of highly regioselective synthetic catalysts, however, is still at an early stage. Discrimination of one site on a molecule from another and distinguishing among many similar molecules presents a difficult and important challenge to both industrial and biological chemistry. See Metalloporphyrins in Catalytic Oxidations; Sheldon, R. A. Ed. Marcel Dekker: New York, 1994). Although the axial ligation properties of simple synthetic metalloporphyrins are well documented in literature, see Bampos, N.; Marvaud, V.; Sanders, J. K. M. Chem. Eur. J. 1998, 4, 325; Stibrany, R. T.; Vasudevan, J.; Knapp, S.; Potenza, J. A.; Emge, T.; Schugar, H. J. J. Am. Chem. Soc. 1996, 118, 3980, size and shape control of ligation to peripherally modified metalloporphyrins has been largely unexplored, with few notable exceptions, where only limited selectivities have been observed. See Bhyrappa, P.; Vaijayanthimala, G.; Suslick, K. S. J. Am. Chem. Soc. 1999, 121, 262; Imai, H.; Nakagawa, S.; Kyuno, E. J. Am. Chem. Soc. 1992, 114, 6719.

The present invention includes the synthesis, characterization and remarkable shape-selective ligation of silyether-metalloporphyrin scaffolds derived from the reaction of 5,10,15,20-tetrakis(2',6'-dihydroxyphenyl)porphyrinatozinc (II) with t-butyldimethylsilyl chloride, whereby the two faces of the Zn(II) porphyrin were protected with six, seven, or eight siloxyl groups. This results in a set of three porphyrins of nearly similar electronics but with different steric encumbrance around central metal atom present in the porphyrin. Ligation to Zn by classes of different sized ligands reveal shape selectivities as large as $10^7$.

Figure 13:
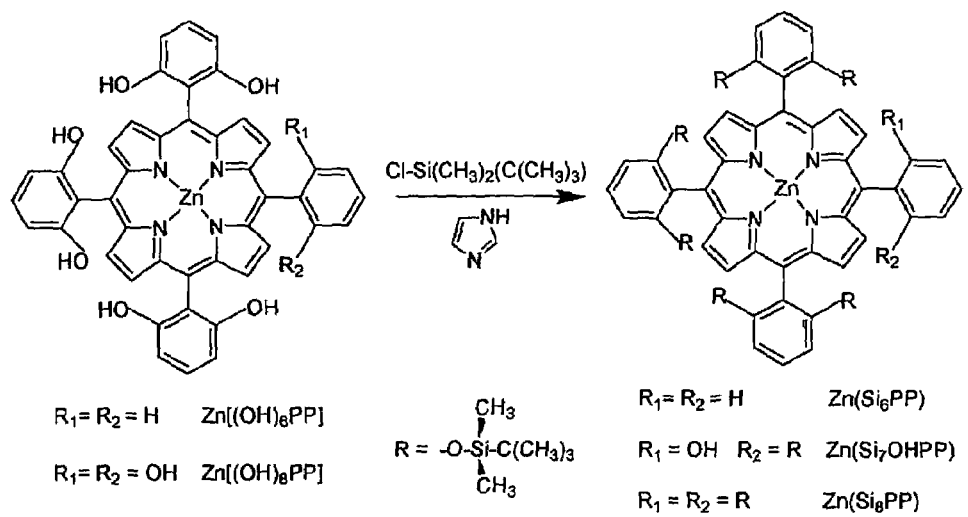
FIG. 13 illustrates the synthesis of siloxyl-substituted bis-pocket porphyrins in accordance with the present invention.

A family of siloxyl-substituted bis-pocket porphyrins were prepared according to the scheme of FIG. 13. The abbreviations of the porhyrins that can be made in accordance with the scheme shown in FIG. 13 are as follows:

Zn(TPP), 5,10,15,20-tetraphenylporphyrinatozinc(II);
Zn[(OH)$_6$PP], 5-phenyl-10,15,20-tris(2',6'-dihydroxyphenyl)porphyrinatozinc(II);
Zn[(OH)$_8$PP], 5,10,15,20-tetrakis(2',6'-dihydroxyphenyl) porphyrinatozinc(II);
Zn(Si$_6$PP), 5(phenyl)-10,15,20-trikis(2',6'-disilyloxyphenyl) porphyrinatozinc(II);
Zn(Si$_7$OHPP), 5,10,15-trikis(2',6'-disilyloxyphenyl)-20-(2'-hydroxy-6'-silyloxyphenyl)porphyrinatozinc(II);
Zn(Si$_8$PP), 5,10,15,20-tetrakis(2',6'-disilyloxyphenyl)porphyrinatozinc(II). The synthesis of Zn[(OH)$_6$PP], Zn(Si$_6$PP), and Zn(Si$_8$PP) is detailed below. Zn[(OH)$_6$PP] and Zn[(OH)$_8$PP] were obtained (see Bhyrappa, P.; Vaijayanthimala, G.; Suslick, K. S. J. Am. Chem. Soc. 1999, 121, 262) from demethylation (see Momenteau, M.; Mispelter, J.; Loock, B.; Bisagni, E. J. Chem. Soc. Perkin Trans. 1, 1983, 189) of corresponding free base methoxy compounds followed by zinc(II) insertion. The methoxy porphyrins were synthesized by acid catalysed condensation of pyrrole with respective benzaldehydes following Lindsey procedures. See Lindsey, J. S.; Wagner, R. W. J. Org. Chem. 1989, 54, 828. Metalation was done in methanol with Zn(O$_2$CCH$_3$)$_2$. The t-butyldimethylsilyl groups were incorporated into the metalloporphyrin by stirring a DMF solution of hydroxyporphyrin complex with TBDMSiCl (i.e., t-butyldimethylsilyl chloride) in presence of imidazole. See Corey, E. J; Venkateswarlu, A. J. Am. Chem. Soc. 1972, 94, 6190. The octa (Zn(Si$_8$PP)), hepta (Zn(Si$_7$OHPP)), and hexa (Zn(Si$_6$PP)) silylether porphyrins were obtained from Zn[(OH)$_8$PP] and Zn[(OH)$_6$PP], respectively. The compounds were purified by silica gel column chromatography and fully characterized by UV-Visible, $^1$H-NMR, HPLC, and MALDI-TOF MS.

The size and shape selectivities of the binding sites of these bis-pocket Zn silylether porphyrins were probed using the axial ligation of various nitrogenous bases of different shapes and sizes in toluene at 25° C. Zn(II) porphyrins were chosen because, in solution, they generally bind only a single axial ligand. Successive addition of ligand to the porphyrin solutions caused a red-shift of the Soret band typical of coordination to zinc porphyrin complexes. There is no evidence from the electronic spectra of these porphyrins for significant distortions of the electronic structure of the porphyrin. The binding constants ($K_{eq}$) and binding composition (always 1:1) were evaluated using standard procedures. See Collman, J. P.; Brauman, J. I.; Doxsee, K. M.; Halbert, T. R.; Hayes, S. E.; Suslick, K. S. J. Am. Chem. Soc. 1978, 100, 2761; Suslick, K. S.; Fox, M. M.; Reinert, T. J. Am. Chem. Soc. 1984, 106,4522. The $K_{eq}$ values of the silylether porphyrins with nitrogenous bases of different classes are compared with the sterically undemanding Zn(TPP) in FIGS. 14a, 14b, and 14c. It is worth noting the parallel between shape selectivity in these equilibrium measurements and prior kinetically-controlled epoxidation and hydroxylation. See Collman, J. P.; Zhang, X. in Comprehensive Supramolecular Chemistry; Atwood, J. L.; Davies, J. E. D.; MacNicol, D. D.; Vogtel, F. Eds.; Pergamon: New York, 1996; vol. 5, pp. 1-32; Suslick, K. S.; van Deusen-Jeffries, S. in Comprehensive Supramolecular Chemistry; Atwood, J. L.; Davies, J. E. D.; MacNicol, D. D.; Vogtel, F. Eds.; Pergamon: New York, 1996; vol. 5, pp. 141-170; Suslick, K. S. in Activation and Functionalization of Alkanes; Hill, C. L., ed.; Wiley & Sons: New York, 1989; pp. 219-241; Bhyrappa, P.; Young, J. K.; Moore, J. S.; Suslick, K. S. J. Am. Chem. Soc., 1996, 118, 5708-5711. Suslick, K. S.; Cook, B. R. J. Chem. Soc., Chem. Comm. 1987,200-202; Cook, B. R.; Reinert, T. J.; Suslick, K. S. J. Am. Chem. Soc. 1986,108,7281-7286; Suslick, K. S.; Cook, B. R.; Fox, M. M. J. Chem. Soc., Chem. Commun. 1985, 580-582. The selectivity for equilibrated ligation appears to be substantially larger than for irreversible oxidations of similarly shaped substrates.

The binding constants of silylether porphyrins are remarkably sensitive to the shape and size of the substrates relative to Zn(TPP). See FIGS. 14a, 14b, and 14c. The binding constants of different amines could be controlled over a range of $10^1$ to $10^7$ relative to Zn(TPP). It is believed that these selectivities originate from strong steric repulsions created by the methyl groups of the t-butyldimethylsiloxyl substituents. The steric congestion caused by these bulky silylether groups is pronounced even for linear amines and small cyclic amines (e.g., azetidine and pyrrolidine).

Figure 14A:
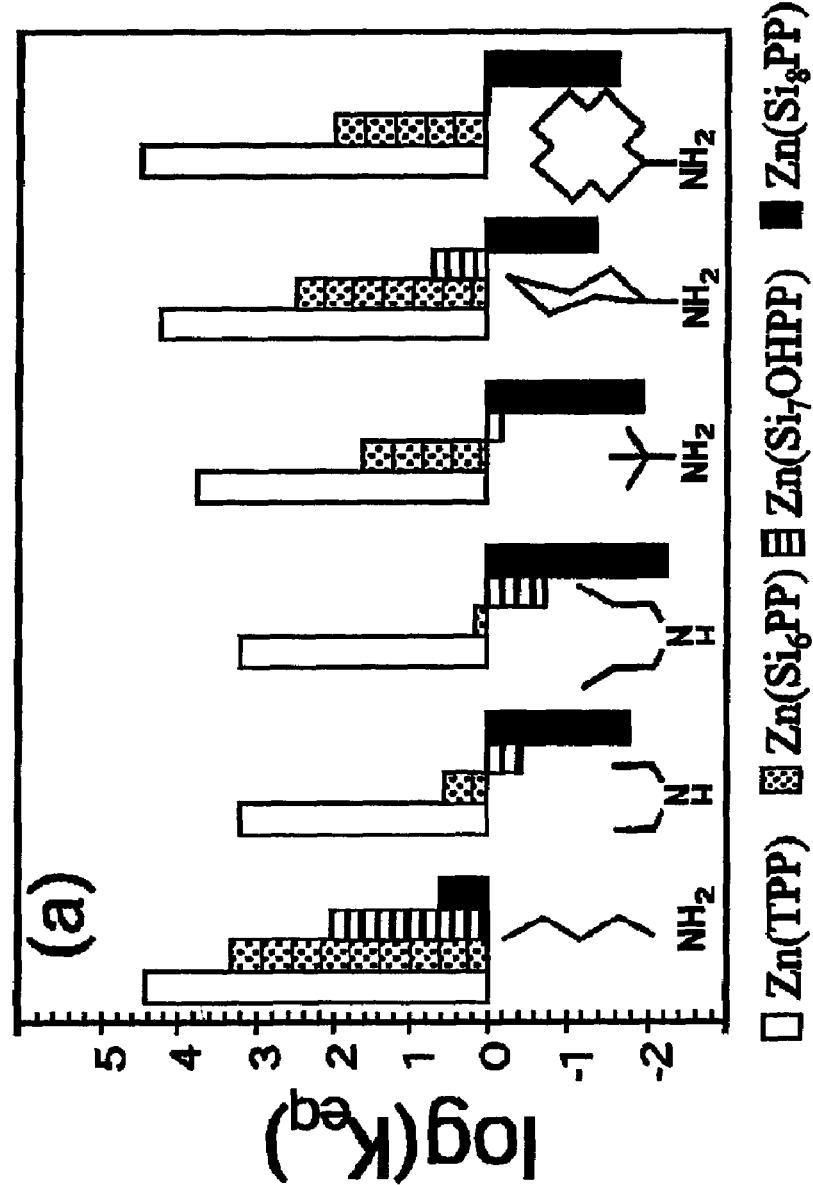

There are very large differences in $K_{eq}$ for porphyrins having three versus four silylether groups on each face (e.g., hexa- vs. octa-silylether porphyrins), as expected based on obvious steric arguments (see FIGS. 14a, 14b, and 14c). Even between the hexa- over hepta-silylether porphyrins, however, there are still substantial differences in binding behavior. It is believed that this is probably due to doming of the macrocycle in the hexa- and hepta-silylether porphyrins, which lessens the steric constraint relative to the octasilylether porphyrin. Such doming will be especially important in porphyrins whose two faces are not identical. The free hydroxy functionality of the hepta-silylether may play a role in binding of bi-functionalized ligands (e.g., free amino acids); for the simple amines presented here, however, we have no evidence of any special effects.

These silylether porphyrins showed remarkable selectivities for normal, linear amines over their cyclic analogues. For a series of linear amines (n-propylamine through n-decylamine), $K_{eq}$ were very similar for each of the silylether porphyrins. In comparison, the relative $K_{eq}$ for linear versus cyclic primary amines (FIG. 14a, n-butylamine vs. cyclohexylamine) were significantly different: $K_{eq}^{linear}/K_{eq}^{cyclic}$ ranges from 1 to 23 to 115 to >200 for Zn(TPP), Zn(Si$_6$PP), Zn(Si$_7$OHPP), and Zn(Si$_8$PP), respectively. The ability to discriminate between linear and cyclic compounds is thus established.

A series of cyclic 2° amines (FIG. 14b) demonstrate the remarkable size and shape selectivities of this family of bis-pocket porphyrins. Whereas the binding constants to Zn(TPP) with those amines are virtually similar. In contrast, the $K_{eq}$ values for silylether porphyrins strongly depend on the ring size and its peripheral substituents. The effect of these shape-selective binding sites is clear, even for compact aromatic ligands with non-ortho methyl substituents (FIG. 14c).

Figure 15:
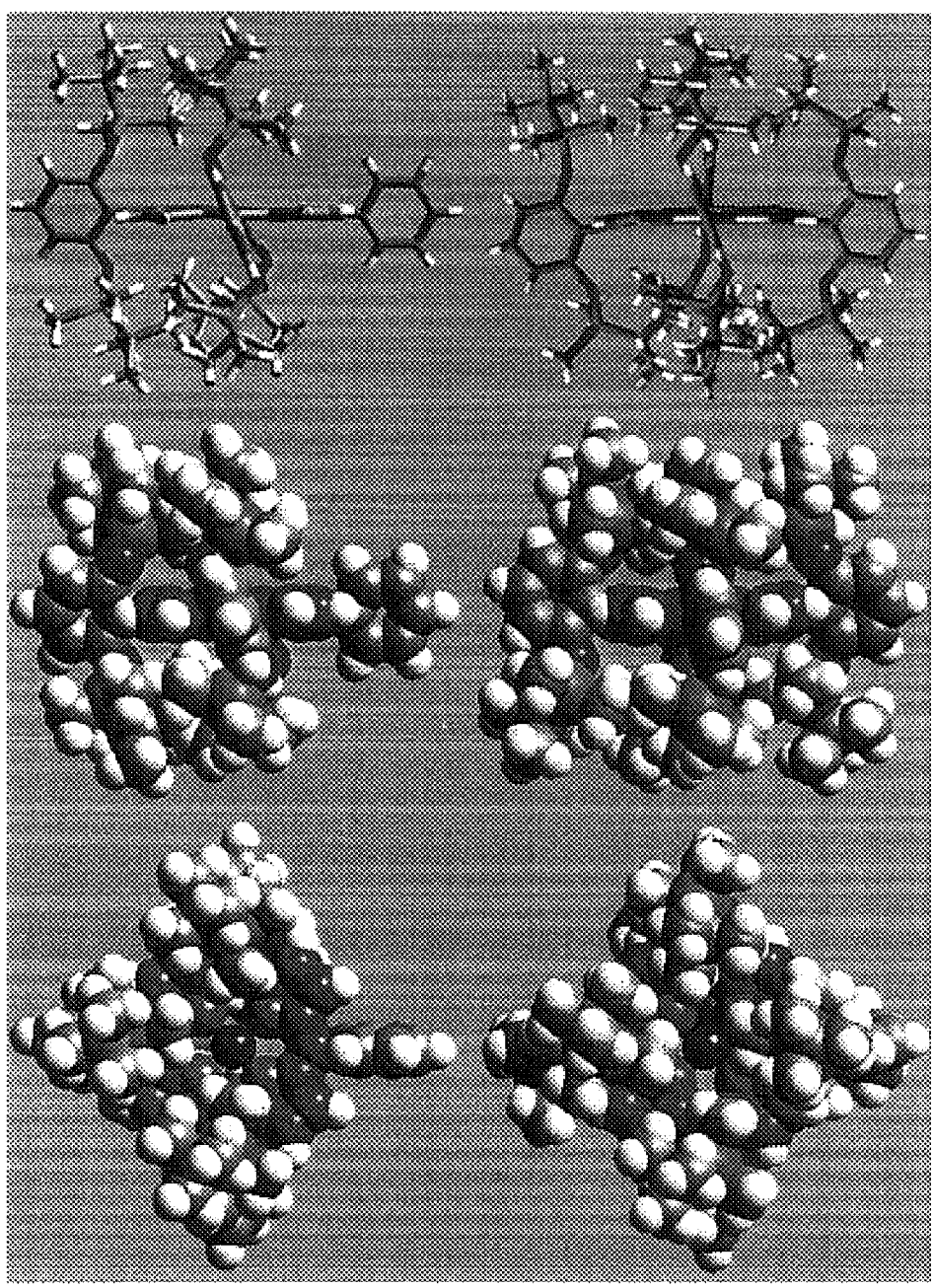
FIG. 15 illustrates molecular models of $Zn(Si_6PP)$ (left column) and $Zn(Si_8PP)$ (right column).

The molecular structures of these silylether porphyrins explains their ligation selectivity. The x-ray single crystal structure of Zn(Si$_8$PP) has been solved in the triclinic P1bar space group. See Single crystal x-ray structure of Zn(Si8PP) shown in FIG. 15. As shown in FIG. 15, Zn(Si$_6$PP) (energy minimized molecular model) and Zn(Si$_8$PP) (single crystal x-ray structure) have dramatically different binding pockets. In the octasilylether porphyrin, the top access on both faces of the porphyrin is very tightly controlled by the siloxyl pocket. In contrast, the metal center of the hexasilylether porphyrin is considerably more exposed for ligation.

FIG. 15 illustrates molecular models of Zn(Si$_6$PP) (left column) and Zn(Si$_8$PP) (right column). The pairs of images from top to bottom are cylinder side-views, side-views, and top-views, respectively; space filling shown at 70% van der Waals radii; with the porphyrin carbon atoms shown in purple, oxygen atoms shown in red, silicon atoms in green, and Zn in dark red. The x-ray single crystal structure of Zn(Si$_8$PP) is shown; for Zn(Si$_6$PP), an energy-minimized structure was obtained using Cerius 2 from MSI.

In summary, a series of bis-pocket siloxyl metalloporphyrin complexes were prepared with sterically restrictive binding pockets on both faces of the macrocycle. Ligation to Zn by various nitrogenous bases of different sizes and shapes were investigated. Shape selectivities as large as $10^7$ were found, compared to unhindered metalloporphyrins. Fine-tuning of ligation properties of these porphyrins was also possible using pockets of varying steric demands. The shape selectivities shown here rival or surpass those of any biological system.

EXAMPLES OF SYNTHESIS OF SUPER STRUCRURES

Synthesis of 5-phenyl-10,15,20-tris(2',6'-dihydroxyphenyl)-porphyrinatozinc(II), Zn[(OH)$_6$PP]:

The free base 5-phenyl-10,15,20-tris(2',6'-dimethoxyphenyl)-porphyrin was synthesized by Lewis acid catalyzed condensation of 2,6-dimethoxybezaldehyde and benzaldehyde with pyrrole (3:1:4 mole ratio) following the Lindsey procedure. See Lindsey, J. S.; Wagner, R. W. J. Org. Chem. 1989, 54, 828. The mixture of products thus formed was purified by silica gel column chromatography (if necessary, using CH$_2$Cl$_2$ as eluant). The isolated yield of the desired product was found to be 7%(wrt pyrrole used). The corresponding hydroxyporphyrins were obtained by demethylation with pyridine hydrochloride. See Momenteau, M.; Mispelter, J.; Loock, B.; Bisagni, E. J. Chem. Soc. Perkin Trans. 1, 1983, 189. After typical work-up known to those skilled in the art, the crude compound was purified by silica gel column chromatography using ethylacetate as eluant. The first fraction was Zn[(OH)$_6$PP], which was collected and the solvent was removed. The yield of the product was 90% (based on starting hydroxyporphryin). $^1$H NMR of H$_2$[(OH)$_6$PP] in acetone-d$_6$ (ppm): 8.96-8.79(m, 8H, b-pyrrole H), 8.24(m, 2H, o-H 5-Phenyl), 8.07 and 8.02(2s, 6H, —OH), 7.83(m, 3H, m,p-H 5-Phenyl), 7.50(t, 3H, p-H hydroxyphenyl), 6.90(d, 6H, m-H hydroxyphenyl), -2.69(s, 2H, imino-H). Elemental analysis, calcd. for C$_{44}$H$_{30}$O$_6$N$_4$.H$_2$O: C=72.5, H=4.4 and N=7.7%. Found C=72.7, H=4.4 and N=7.4%. The compound showed molecular ion peak at 711 (m/z calcd. for C$_{44}$H$_{30}$O$_6$N$_4$=710) in FAB-MS.

The Zn derivative was obtain by stirring methanol solution of H$_2$[(OH)$_6$PP] with excess Zn(O$_2$CCH$_3$)$_2$2H$_2$O for 1 hour. Methanol was evaporated to dryness and the residue was dissolved in ethylacetate, washed with water, and the organic layer passed through anhyd. Na$_2$SO$_4$. The concentrated ethylacetate solution was passed through a silica gel column and the first band was collected as the desired product. The yield of the product was nearly quantitative. $^1$H NMR of Zn(OH)$_6$PP in acetone-d$_6$ (ppm): 8.95-8.79(m, 8H, b-pyrrole H), 8.22(m, 2H, o-H 5-Phenyl), 7.79(m, 3H, m,p-H 5-Phenyl), 7.75 and 7.65(2s, 6H, —OH), 7.48(t, 3H,p-H hydroxyphenyl), 6.88(d, 6H, m-H hydroxyphenyl). Elemental analysis, calcd. for ZnC$_{44}$H$_{28}$O$_6$N$_4$.H$_2$O: C=66.7, H=3.8, N=7.1 and Zn=8.3%. Found C=66.4, H=3.8, N=6.7 and Zn=8.2%. The compound showed molecular ion peak at 774 (m/z calcd. for ZnC$_{44}$H$_{28}$O$_6$N$_4$=773) in FAB-MS.

Synthesis of 5-phenyl-10,15,20-tris(2',6'-disilyloxyphenyl)-porphyrinatozinc(II), Zn(Si$_6$PP):

The hexasilylether porphyrin was synthesized by stirring a DMF solution of 5-phenyl-10,15,20-tris(2',6'-dihydroxyphenyl)-porphyrinatozinc(II) (100 mg, 0.13 mmol) with t-butyldimethyl silylchloride (1.18 g, 7.8 mmol) in presence of imidazole (1.2 g, 17.9 mmol) at 60° C. for 24 h under nitrogen. After this period the reaction mixture was washed with water and extracted in CHCl$_3$. The organic layer was dried over anhyd. Na$_2$SO$_4$. The crude reaction mixture was loaded on a short silica gel column and eluted with mixture of CHCl$_3$/petether (1:1, v/v) to get rid of unreacted starting material and lower silylated products. The desired compound was further purified by running another silica gel column chromatography using mixture of CHCl$_3$/petether (1:3, v/v) as eluant. The yield of the product was 60% based on starting hydroxyporphyrin.

$^1$H NMR in chloroform-d (ppm): 8.94-8.82(m, 8H, b-pyrrole H), 8.20(m, 2H, o-H 5-Phenyl), 7.74(m, 3H, m,p-H 5-Phenyl), 7.49(t, 3H, p-H hydroxyphenyl), 6.91(t, 6H, m —H hydroxyphenyl), −0.02 and −0.34(2s, 54H, t-butyl H), −0.43, −0.78 and −1.01(3s, 36H, methyl H). Elemental analysis, calcd. for ZnC$_{80}$H$_{112}$O$_6$N$_4$Si$_6$: C=65.8, H=7.7, N=3.8, Si=11.5 and Zn=4.5%. Found C=65.5, H=7.7, N=3.8, Si=11.2 and Zn=4.4%. The low resolution MALDI-TOF mass spectrum showed molecular ion peak at 1457 (m/z calcd. for ZnC$_{80}$H$_{112}$O$_6$N$_4$Si$_6$=1458).

Synthesis of 5,10,15-tris(2',6'-disilyoxyphenyl)-20-(2'-hydr-oxy-6'-silyloxyphenyl)porphyrinatozinc(II), [Zn(Si$_7$OHPP)], and 5,10,15,20-tetrakis(2',6'-disilyloxyphenyl)porphy-rinato-zinc(II), [Zn(Si$_8$PP)]:

The synthesis of precursor porphyrin 5,10,15,20-tetrakis-(2',6'-dihydroxyphenyl)porphyrin and its Zn derivative was accomplished as reported earlier. See Bhyrappa, P.; Vaijayanthimala, G.; Suslick, K. S. J. Am. Chem. Soc. 1999, 121, 262. The hepta-and octa-silylether porphyrins were synthesized by stirring DMF solution of 5,10,15,20-tetrakis(2',6'-dihydroxyphenyl)porphyrinatozinc(II) (100 mg, 0.12 mmol) with t-butyldimethyl silylchloride (1.45 g, 9.6 mmol) in presence of imidazole (1.50 g, 22.1 mmol) at 60° C. for 24 h under nitrogen. After usual work-up the mixture of crude products were loaded on a silica gel column and eluted with mixture of CHCl$_3$/pet. ether (1:1, v/v) to remove unreacted starting material and lower silylated products. The major product isolated from this column is a mixture of hepta- and octa-silylated porphyrins. The mixture thus obtained was further purified by another silica gel column chromatography using mixture of CHCl$_3$/pet. ether (1:3, v/v) as eluant. The first two bands were isolated as octa- and hepta-silylether porphyrin at 45% and 30% yield, respectively. Both the compounds were characterized by UV-Visible, $^1$H NMR and MALDI-TOF spectroscopic techniques. The homogeneity of the sample was verified by HPLC.

For Zn(Si$_7$OHPP), $^1$H NMR in chloroform-d (ppm): 8.91(m, 8H, b-pyrrole H), 7.50(m, 4H, p-H), 7.01-6.81(m, 8H, m-H), 0.11 to −0.03(12s, 105H, t-butyl and methyl H). Elemental analysis, calcd. for ZnC$_{86}$H$_{126}$O$_8$N$_4$Si$_7$: C=64.3, H=7.8, N=3.5, Si=12.3 and Zn=4.1%. Found C=63.6, H=8.1, N=3.5, Si=12.1 and Zn=3.9%. The low resolution MALDI-TOF mass spectrum showed molecular ion peak at 1604 (m/z calcd. for ZnC$_{86}$H$_{126}$O$_8$N$_4$Si$_7$=1604).

For Zn(Si$_8$PP), $^1$H NMR in chloroform-d (ppm): 8.89(s, 8H, b-pyrrole H), 7.49(t, 4H, p-H), 6.92(d, 8H, m-H), 0.09(s, 72H, t-butyl H), −1.01(s, 48H, methyl H). Elemental analysis, calcd. for ZnC$_{92}$H$_{140}$O$_8$N$_4$Si$_8$: C=64.2, H=8.1, N=3.3, Si=13.1 and Zn=3.8%. Found C=63.5, H=8.4, N=3.3, Si=12.8 and Zn=4.0%. The low resolution MALDI-TOF mass spectrum showed molecular ion peak at 1719 (m/z calcd. for ZnC$_{92}$H$_{140}$O$_8$N$_4$Si$_8$=1718).

ADDITIONAL FEATURES OF THE PREFERRED EMBEDIMENTS OF THE INVENTION

Having demonstrated electronic differentiation and shape-selective distinction of analytes that bind to metal ions in metallodyes, an important further goal is the differentiation of analytes that do not bind or bind only weakly to metal ions. Such analytes include acidic compounds, such as carboxylic acids, and certain organic compounds lacking ligatable functionality, such as simple alkanes, arenes, some alkenes and alkynes (especially if sterically hindered), and molecules sterically hindered as to preclude effective ligation. One approach that has been developed to achieve this goal in accordance with the present invention is to include in the sensor array other chemoresponsive dyes, including pH sensitive dyes (i.e., pH indicator or acid-base indicator dyes that change color upon exposure to acids or bases), and/or solvatochromic dyes (i.e., dyes that change color depending upon the local polarity of their micro-environment).

It has been discovered that the addition of pH sensitive dyes and solvatochromic dyes to other arrays containing metalloporphyrins as described above expands the range of analytes to which the arrays are sensitive, improves sensitivities to some analytes, and increases the ability to discriminate between analytes.

The present invention includes an artificial nose comprising an array, the array comprising at least a first dye and a second dye deposited directly onto a single support in a predetermined pattern combination, the combination of the dyes in the array having a distinct and direct spectral absorbance or reflectance response to an analyte wherein the first dye and the second dye are selected from the group consisting of chemoresponsive dyes, and the second dye is distinct from the first dye. In a preferred embodiment, the first dye is selected from the group consisting of porphyrin, chlorin, chlorophyll, phtahlocyanine, and salen and their metal complexes. In another preferred embodiment, the second dye is selected from the group of dyes consisting of acid-base indicator dyes and solvatochromic dyes.

The present invention includes a method of detecting an analyte comprising the steps of: (a) forming an array of at least a first dye and a second dye deposited directly onto a single support in a predetermined pattern combination, the combination of the dyes in the array having a distinct and direct spectral absorbance or reflectance response to an analyte wherein the first dye and the second dye are selected from the group consisting of chemoresponsive dyes, and the second dye is distinct from the first dye; (b) subjecting the array to an analyte; (c) inspecting the array for a distinct and direct spectral absorbance or reflectance response; and (d) correlating the distinct and direct spectral response to the presence of the analyte. In a preferred method, the first dye is selected from the group consisting of porphyrin, chlorin, chlorophyll, phtahlocyanine, and salen and their metal complexes. In another preferred method, the second dye is selected from the group of acid-base indicator dyes and solvatochromic dyes.

The present invention includes an artificial tongue comprising an array, the array comprising at least a first dye and a second dye deposited directly onto a single support in a predetermined pattern combination, the combination of the dyes in the array having a distinct and direct spectral absorbance or reflectance response to an analyte wherein the first dye and the second dye are selected from the group consisting of chemoresponsive dyes, and the second dye is distinct from the first dye. In a preferred embodiment, the first dye is selected from the group consisting of porphyrin, chlorin, chlorophyll, phtahlocyanine, and salen and their metal complexes. In another preferred embodiment, the second dye is selected from the group of dyes consisting of acid-base indicator dyes and solvatochromic dyes.

Chemoresponsive dyes are those dyes that change color, in either reflected or absorbed light, upon changes in their chemical environment. Three general classes of chemoresponsive dyes are (1) Lewis acid/base dyes, (2) pH indicator dyes, and (3) solvatochromic dyes.

Lewis acid/base dyes are those dyes that contain a Lewis acidic or basic center (where a Lewis acid is an electron pair acceptor and a Lewis base is an electron pair donor) and change color in response to changes in the Lewis acidity or basicity of their environment. A specific set of Lewis acid/base dyes includes dyes such as porphyrin, chlorin, chlorophyll, phtahlocyanine, and salen and their metal complexes.

pH indicator or acid-base indicator dyes are those that change color in response to changes in the proton acidity or basicity (also called Bronsted acidity or basicity) of their environment. A specific set of pH indicator dyes include Chlorphenol Red, Bromocresol Green, Bromocresol Purple, Bromothymol Blue, Phenol Red, Thymol Blue, Cresol Red, Alizarin, Mordant Orange, Methyl Orange, Methyl Red, Congo Red, Victoria Blue B, Eosin Blue, Fat Brown B, Benzopurpurin 4B, Phloxine B, Orange G, Metanil Yellow, Naphthol Green B, Methylene Blue, Safranine O, Methylene Violet 3RAX, Sudan Orange G, Morin Hydrate, Neutral Red, Disperse Orange 25, Rosolic Acid, Fat Brown RR, Cyanidin chloride, 3,6-Acridineamine, 6'-Butoxy-2,6-diamino-3,3'-azodipyridine, para-Rosaniline Base, Acridine Orange Base, Crystal Violet, and Malachite Green Carbinol Base.

Solvatochromic dyes are those that change color in response to changes in the general polarity of their environment, primarily through strong dipole-dipole interactions. To some extent, all dyes inherently are solvatochromic, although some are much more responsive than others. A specific set of highly responsive solvatochromic dyes include Reichardt's Dye and Nile Red.

It has been discovered that the following pH indicator (i.e., acid-base indicator) dyes and solvatochromic dyes are useful to expand the range of analytes to which the arrays containing metalloporphyrins are sensitive, improve sensitivities to some analytes, and increase the ability to discriminate between analytes. Those skilled in the art will recognize that other modifications and variations in the choice of such auxiliary dyes may be made in addition to those described and illustrated herein without departing from the spirit and scope of the present invention. Accordingly, the choice of dyes described and illustrated herein should be understood to be illustrative only and not limiting upon the scope of the present invention.

Chlorphenol Red
Molecular Formula: $C_{19}H_{12}Cl_2O_5S$
Molecular Weight: 423.28
CAS: 4430-20-0
Transition interval: pH 4.8 (yellow) to pH 6.7 (violet)

Bromocresol Green
Synonyms: 3',3",5',5"Tetrabromo-m-cresolsulfonphthalein; Bromcresol Green
Molecular Formula: $C_{21}H_{14}Br_4O_5S$
Molecular Weight: 698.04
CAS: 76-60-8

$$pH = 3.8 \text{ yellow}$$
$$= 5.4 \text{ blue}$$

Bromocresol Purple
Synonyms: 5',5" dibromo-m-cresolsulfonphthalein; Bromcresol Purple
Molecular Formula: $C_{21}H_{16}Br_2O_5S$
Molecular Weight: 698.04
CAS: 115-40-2

$$pH = 5.2 \text{ yellow}$$
$$= 6.8 \text{ blue}$$

Bromothymol Blue
Synonyms: 3',3"-Dibromothymolsulfonphthalein; Bromthymol Blue
Molecular Formula: $C_{27}H_{28}Br_2O_5S$
Molecular Weight: 624.41
CAS: 76-59-5

$$pH = 6.0 \text{ yellow}$$
$$= 7.6 \text{ blue}$$

Phenol Red
Synonyms: Phenolsulfonphthalein
Molecular Formula: $C_{19}H_{14}O_5S$
Molecular Weight: 354.38
CAS: 143-74-8

$$pH = 6.8 \text{ yellow}$$
$$= 8.2 \text{ red}$$

Thymol Blue
Synonyms: Thymolsulfonphthalein
Molecular Formula: $C_{27}H_{30}O_5S$
Molecular Weight: 466.60
CAS: 76-61-9

$$pH = 1.2 \text{ red}$$
$$= 2.8 \text{ yellow}$$
$$= 8 \text{ yellow}$$
$$= 9.2 \text{ blue}$$

Cresol Red
Synonyms: Phenol, 4,4'-(1,1-dioxido-3H-2,1-benzoxathiol-3-ylidene)bis[2-methyl-(9CI)]
Molecular Formula: $C_{21}H_{18}O_5S$
Molecular Weight: 382.43
CAS: 1733-12-6 pH 1.8 (orange) to pH 2.0 (yellow); Transition interval (alkaline): pH 7.0 (yellow) to pH 8.8 (violet)

Alizarin
Synonyms: 1,2-Dihydroxyanthraquinone, 9,10-Anthracenedione, 1,2-dihydroxy-(9CI)
Molecular Formula: $C_{14}H_8O_4$
Molecular Weight: 240.22 pH = 5.5 yellow
= 6.8 red
= 10.1 red
= 12.1 violet

Mordant Orange 1
Synonyms: Alizarin Yellow R, C.I. 14030, 5-(4-nitrophenylazo)salicylic acid
Molecular Formula: $C_{13}H_9N_3O_5$
Molecular Weight: 287.23
CAS: 2243-76-7

Methyl Orange
Synonyms: 4-(p-[Dimethylamino]phenylazo)benzenesulfonic acid, sodium salt Acid Orange 52
Molecular Formula: $C_{14}H_{14}N_3O_3SNa$
Molecular Weight: 327.3
pH 3.0 (pink)—pH 4.4 (yellow)

Methyl Red
Synonyms: 4-Dimethylaminoazobenzene-2'carboxylicacid; 2-(4-Dimethylaminophenylazo)benzoic acid
Molecular Formula: $C_{15}H_{15}N_3O_2$
Molecular Weight: 269.31
CAS: 493-52-7 pH = 4.2 pink
= 6.2 yellow

Reichardt's Dye
Synonyms: [2,6-diphenyl-4-(2,4,6-triphenylpyridinio)phenolate]
Molecular Formula: $C_{41}H_{29}NO$
Molecular Weight: 551.69
CAS: 10081-39-7

Nile Red
Synonyms: 5H-Benzo[a]phenoxazin-5-one, 9-(diethylamino)-(7CI, 8CI, 9CI), 9-(Diethylamino)-5H-benzo[a]phenoxazin-5-one; Nile Blue A oxazone
Molecular Formula: $C_{20}H_{18}N_2O_2$
Molecular Weight: 318.38
CAS: 7385-67-3

Congo Red
Molecular Formula: $C_{32}H_{24}N_6O_6S_2.Na_2$
Molecular Weight: 696.67
CAS: 573-58-0
pH range: blue 3.1-4.9 red Victoria Blue B
Synonyms: Basic Blue 26, C.I. 44045
Molecular Formula: $C_{33}H_{32}ClN_3$
Molecular Weight: 506.10
CAS: 2580-56-5

Eosin Blue
Synonyms: (Acid Red 91, C.I. 45400, 4',5'-dibromo-2',7'-dinitrofluorescein, disodium salt)
Molecular Formula: $C_{20}H_8Br_2N_2O_9$
Molecular Weight: 624.08
CAS: 548-24-3

Fat Brown B
Synonyms: Solvent red 3
Molecular Formula: $C_{18}H_{16}N_2O_2$
Molecular Weight: 292.3
CAS: 6535-42-8

Benzopurpurin 4B
Synonyms: (C.I. 23500, Direct Red 2)
Molecular Formula: $C_{34}H_{28}N_6O_6S_2$
Molecular Weight: 724.73
CAS: 992-59-6 pH range: violet 1.2-3.8 yellow

Phloxine B
Molecular Formula: $C_{20}H_4Br_4Cl_4O_5$
CAS: 18472-87-2 pH range: colorless 2.1-4.1 pink

Orange G
Synonyms: 1-Phenylazo-2-naphthol-6,8-disulfonic acid disodium salt
Molecular Formula: $C_{16}H_{10}N_2Na_2O_7S_2$
Molecular Weight: 452.

pH range: yellow 11.5-14.0 pink

Metanil Yellow
Synonyms: (Acid Yellow 36, C.I. 13065)
Molecular Formula: $C_{18}H_{15}N_3O_3S.Na$
Molecular Weight: 375.38
CAS: 587-98-4
pH 1.5 (red) to pH 2.7 (yellow)

Naphthol Green B
Synonyms: (Acid Green 1, C.I. 10020)
Molecular Formula: $C_{10}H_7NO_5S$
Molecular Weight: 878.47
CAS: 19381-50-1

Methylene Blue
Synonyms: (Basic Blue 9, C.I. 52015)
Molecular Formula: $C_{16}H_{18}ClN_3S$
Molecular Weight: 373.90
CAS: 7220-79-3

Safranine O
Synonyms: (C.I. 50240, 3,7-diamino-2,8-dimethyl-5-phenylphenazinium chloride)
Molecular Formula: $C_{20}H_{19}ClN_4$
Molecular Weight: 350.85
CAS: 477-73-6

Methylene Violet 3RAX
Synonyms: [3-amino-7-(diethylamino)-5-phenylphenazinium chloride, C.I. 50206, N,N-diethylphenosafranine]
Molecular Formula: $C_{22}H_{23}ClN_4$
Molecular Weight: 378.91
CAS: 4569-86-2

Sudan Orange G
Synonyms: [C.I. 11920, 4-(phenylazo)resorcinol, Solvent Orange 1]
Molecular Formula: $C_6H_5N=NC_6H_3-1,3-(OH)_2$
Molecular Weight: 214.22
CAS: 2051-85-6

Morin Hydrate
Synonyms: (2',3,4',5,7-pentahydroxyflavone)
Molecular Formula: $C_{15}H_{10}O_7$
Molecular Weight: 302.24 Neutral Red Molecular Formula: $C_{15}H_{16}N_4 \cdot HCl$
Molecular Weight: 288.78
CAS: 553-24-2 pH = 6.8 red
= 8.0 yellow

Disperse Orange 25
Molecular Formula: $C_{17}H_{17}N_5\ O_2$
Molecular Weight: 323.36
CAS: 31482-56-1

Rosolic Acid
Molecular Formula: $C_{20}H_{16}O_3$
Molecular Weight: 290.32
CAS: 603-45-2 pH = 5.0 yellow
= 6.8 pink

Fat Brown RR
Molecular Formula: $C_{16}H_{14}N_4$
Molecular Weight: 262.32
CAS: 6416-57-5

Cyanidin chloride
Molecular Formula: C15H11O6.Cl
Molecular Weight: 322.7
CAS: 528-58-5

3,6-Acridineamine
Molecular Formula: $C_{13}H_{11}N_3$
Molecular Weight: 209.25
CAS Number: 92-62-6

6'-Butoxy-2,6-diamino-3,3'-azodipyridine
Synonym: Azodipyridine
Molecular Formula: $C_{14}H_{18}N_6O$
Molecular Weight: 286.34
CAS: 617-19-6 para-Rosaniline Base
Synonym: Rosaniline
Molecular Formula: $C_{19}H_{19}N_3O$
Molecular Weight: 305.4
CAS: 25620-78-4

Acridine Orange Base
Molecular Formula: $C_{17}H_{19}N_3$
Molecular Weight: 265.36
CAS: 494-38-2

Crystal Violet
Molecular Formula: $C_{25}H_{30}N_3 \cdot Cl$
Molecular Weight: 407.99
CAS: 548-62-9 pH = 0 yellow
= 1.8 blue

Malachite Green Carbinol Base
Molecular Formula: $C_{23}H_{26}N_2O$
Molecular Weight: 346.48
CAS: 510-13-4 pH = 0.2 yellow
= 1.8 blue-green

In a preferred embodiment, a low volatility liquid, e.g., a plasticizer, is used in an array of the present invention to keep the dyes in the array from crystallizing and to enhance then response of the array to an analyte. Examples of suitable low volatility liquids include, but are not limited to DOW CORNING 704 silicone diffusion pump fluid (Molecular Weight: 484.82, Density: 1.070, CAS Number: 3982-82-9), and diundecyl phthalate (Molecular Weight: 474.73, Density: 0.950, CAS Number: 3648-20-2, Formula: $C_{30}H_{50}O_4$, Boiling Point (° C.): 523 at 760 torr), dibutyl phthalate (Molecular Weight: 278.4, Density: 1.048, CAS Number: 84-74-2, Formula: $C_{16}H_{22}O_4$, Boiling Point (° C.): 340 at 760 torr), diisopropyl phthalate (Molecular Weight: 250.3, Density: 1.063, CAS Number: 605-45-8, Formula: $C_{14}H_{18}O_4$), squalane (Molecular Weight: 422.83, Density: 0.810, CAS Number: 111-01-3, Formula: $C_{30}H_{62}$, Boiling Point (° C.): 176 at 0.05 torr), triethylene glycol dimethyl ether (synonym: Trigluyme, Molecular Weight: 178.23, Density: 0.986, CAS Number: 112-49-2, Formula: $C_8H_{18}O_4$, Boiling Point (° C.): 216 at 760 torr), and tetraethylene glycol dimethyl ether (synonym: Tetraglyme, (Molecular Weight: 222.28, Density: 1.009, CAS Number: 143-24-8, Formula: $C_{10}H_{22}O_5$, Boiling Point (° C.): 275-276 at 760 torr).

Figure 16:
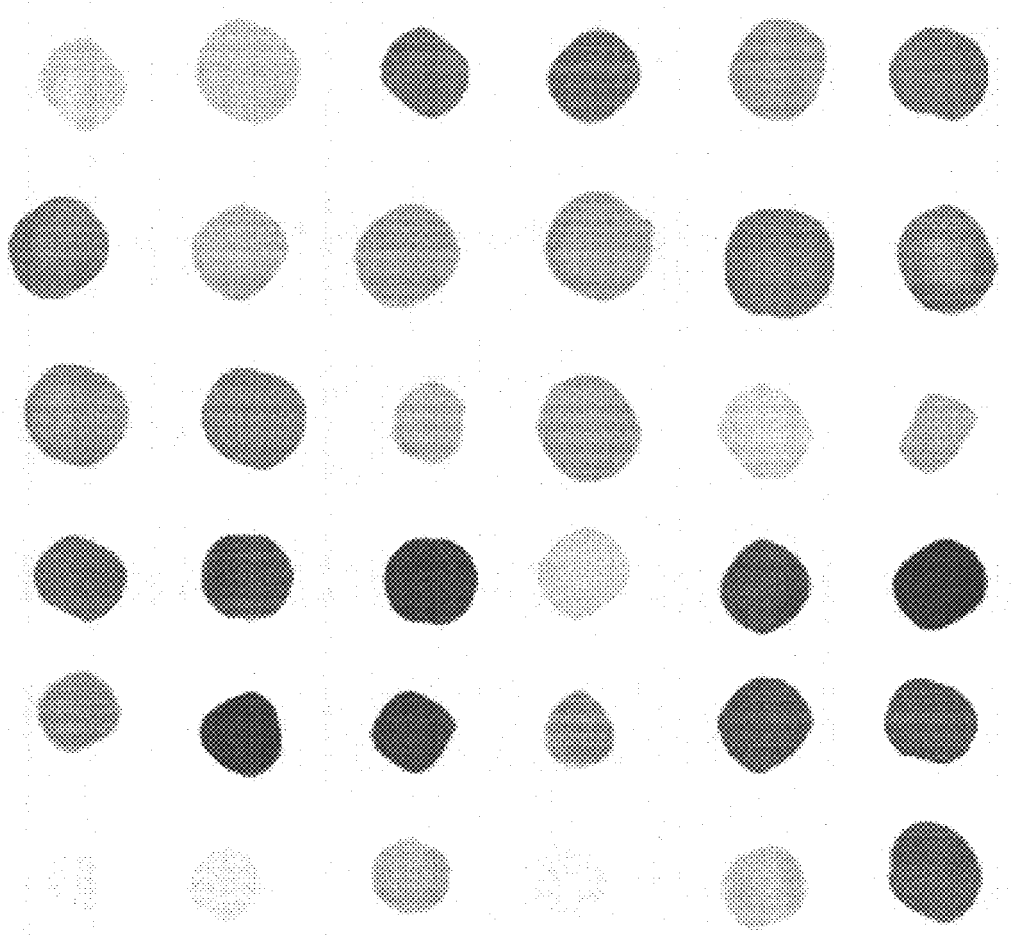
FIG. 16 illustrates an array containing illustrative examples of porphyrin, metalloporphyrin, acid-base indicator, and solvatochromatic dyes.

FIG. 16 illustrates an array containing illustrative examples of porphyrin, metalloporphyrin, acid-base indicator, and solvatochromic dyes. Typical sizes can range from 0.5 mm to 2 cm on a side. Linear, hexagonal, or rectangular arrays are also easily used. From left to right and top to bottom the identities and colors of the dyes used in the illustrative example of FIG. 16 are listed in Table 11 as follows (the exact colors depend, among other things, upon scanner settings).

TABLE 11

(Summarizing the Dyes and Colors in FIG. 16, i.e., "Dye - Color")

| | | | | | |
|---|---|---|---|---|---|
| SnTPPCl$_2$ - Light Green | CoTPP - Peach | CrTPPCl - Green | MnTPPCl - Green | FeTPPCl - Light Brownish Green | CuTPP - Salmon |
| AgTPP - Salmon | NiTPP - Pink | InTPPCL - Tan | IrTPPCl - Pink | ZnTPP - Salmon | FeTFPPCl - Olive |
| ZnSi$_6$PP - Pink | ZnSi$_7$OHPP - Deep Pink | ZnSi$_8$PP - Pink | H$_2$TPP - Carmel | H$_2$FPP - Light Brown | Alizarin basic - Violet |
| Me Red - Orange | BCP - Dark Green | BCPbasic - Blue | BTB - Dark Yellow | BTB basic - Blue | Ph Red basic - Lavender |

TABLE 11-continued (Summarizing the Dyes and Colors in FIG. 16, i.e., "Dye - Color")

| | | | | | |
|---|---|---|---|---|---|
| Nile Red - Violet | BCG - Blue | BCG basic - Blue | CresRed - Brownish Purple | CresRed basic - Purple | CP Red - Purple |
| R Dye - Light Blue | TB - Yellow | TB basic - Greenish Gray | MeOr - Yellow | MeOr basic - Orangish Brown | CP Red basic - Bluish Purple | where TPP=5,10,15,20-tetraphenylporphyrinate(-2);
Zn (Si$_6$PP)=5(phenyl)-10,15,29-trikis(2',6'-disilyloxyphenyl)porphyrinatozinc(II);
Zn(Si$_7$OHPP)=5,10,15trikis(2',6'-disilyloxyphenyl)-20-(2'-hydroxy-6'-silyloxyphenyl)porphyrinatozinc(II);
Zn(Si$_8$PP)=5,10,15,20-tetrakis(2',6'-disilyloxyphenyl)porphyrinatozinc(II);
Me Red=Methyl Red;
BCP=Bromocresol Purple;
BTB=Bromothymol Blue;
Ph Red=Phenol Red;
BCG=Bromocresol Green;
CresRed=Cresol Red;
CP Red=Chlorophenol Red;
R Dye=Reichardt's Dye;
TB=Thymol Blue;
MeOr=Methyl Orange; and
basic indicates the addition of KOH until the color of the basic form of the indicator dye was observed.

Note: DOW CORNING 704 silicone diffusion pump fluid (Molecular Weight: 484.82, Density: 1.070, CAS Number: 3982-82-9) was added to all porphyrin solutions: 40 µl/ml.

Figure 17:
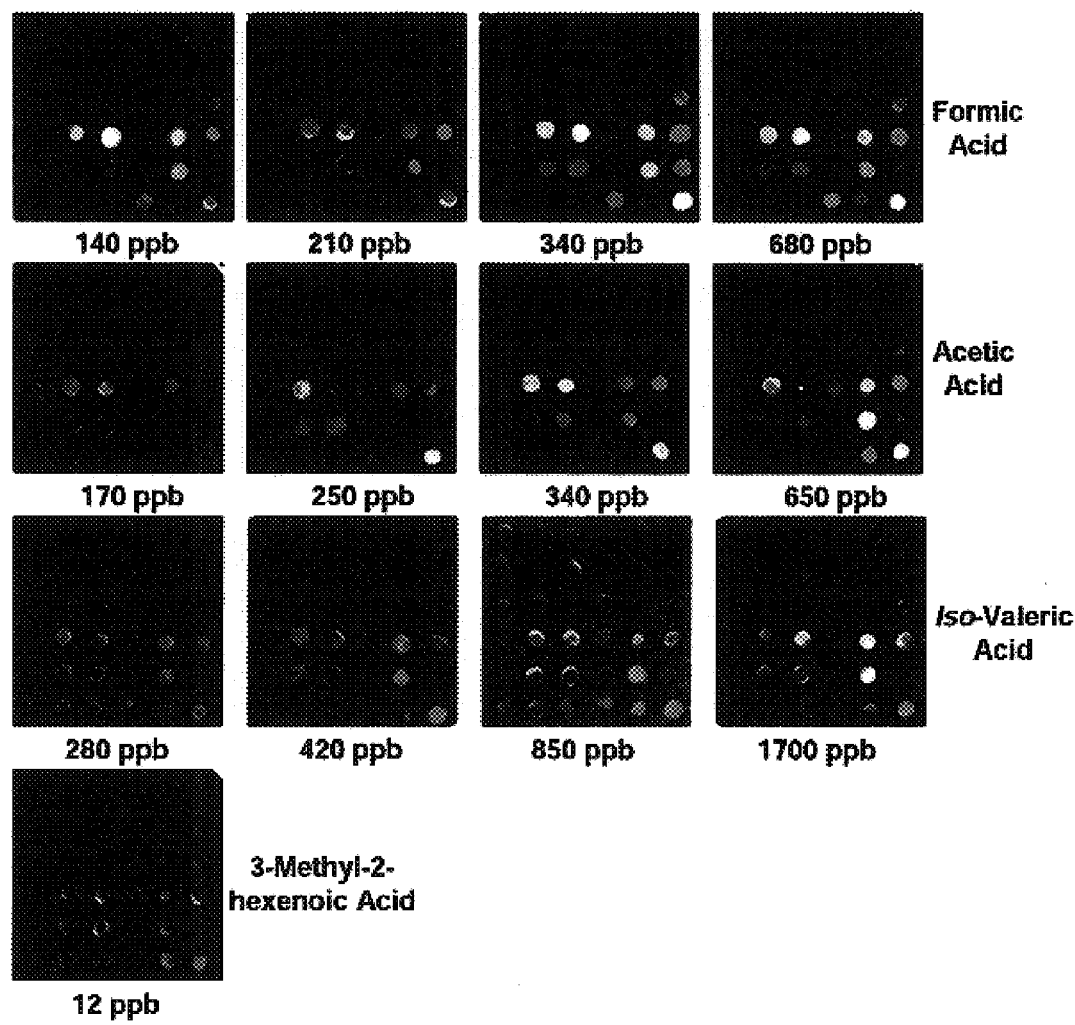
FIG. 17 illustrates the response of the array described in FIG. 16 to acid vapors, specifically formic acid, acetic acid, iso-valeric acid, and 3-methyl-2-hexenoic acid.

FIG. 17 illustrates the response of the array described in FIG. 16 to acid vapors, specifically formic acid, acetic acid, iso-valeric acid, and 3-methyl-2-hexenoic acid. As shown in FIG. 17 and summarized in Table 12 below, the color changes of each dye in response to a particular analyte are shown as color difference maps, as follows (the exact colors depend, among others things, upon scanner settings). The color changes are derived simply by comparing the before exposure and after exposure colors and subtracting the two images (i.e., the absolute value of the difference of the red values becomes the new red value in the color difference map; etc. for green values and blue values). If there is no change in the red, green, and blue color values of a dye in the after-exposure image, then the color difference map will show black (i.e., red value=green value=blue value=0).

TABLE 12

(Summarizing the Dyes and Color Changes in FIG. 17, i.e. "Dye - Difference Map Color")

(Analyte: Formic Acid 140 ppb)

| | | | | | |
|---|---|---|---|---|---|
| SnTPPCl$_2$ - Black (no change) | CoTPP - Black (no change) | CrTPPCl - Black (no change) | MnTPPCl Black (no change) | FeTPPCl - Faint Blue Periphery | CuTPP - Black (no change) |
| AgTPP - Black (no change) | NiTPP - Black (no change) | InTPPCL - Black (no change) | IrTPPCl - Black (no change) | ZnTPP - Black (no change) | FeTFPPCl - Black (no change) |
| ZnSi$_6$PP - Black (no change) | ZnSi$_7$OHPP - Black (no change) | ZnSi$_8$PP - Black (no change) | H$_2$TPP - Black (no change) | H$_2$FPP - Black (no change) | Alizarin basic - Dark Blue |
| Me Red - Black (no change) | BCP - Yellow | BCP basic - White | BTB - Black (no change) | BTB basic - Red Periphery w/Yellow Center | Ph Red basic - Green |
| Nile Red - Black (no change) | BCG - Black (no change) | BCG basic - Dark Purple | CresRed - Black (no change) | CresRed basic - Light Green | CP Red - Black (no change) |
| R Dye - Black (no change) | TB - Black (no change) | TB basic - Black (no change) | MeOr - Green and Purple | MeOr basic - Dark Purple | CP Red basic - Yellow Periphery and Purple center |

(Analyte: Formic Acid 210 ppb)

| | | | | | |
|---|---|---|---|---|---|
| SnTPPCl$_2$ - Black (no change) | CoTPP - Black (no change) | CrTPPCl - Black (no change) | MnTPPCl Black (no change) | FeTPPCl - Black (no change) | CuTPP - Black (no change) |
| AgTPP - Black (no change) | NiTPP - Black (no change) | InTPPCL - Black (no change) | IrTPPCl - Black (no change) | ZnTPP - Black (no change) | FeTFPPCl - Black (no change) |

TABLE 12-continued (Summarizing the Dyes and Color Changes in FIG. 17, i.e. "Dye - Difference Map Color")

| | | | | | |
|---|---|---|---|---|---|
| ZnSi₆PP - Black (no change) | ZnSi₇OHPP - Black (no change) | ZnSi₈PP - Black (no change) | H₂TPP - Black (no change) | H₂FPP - Black (no change) | Alizarin basic - Black (no change) |
| Me Red - Black (no change) | BCP - Red | BCP basic - Yellow Periphery and Red Center | BTB - Black (no change) | BTB basic - Red | Ph Red basic - Green |
| Nile Red - Black (no change) | BCG - Black (no change) | BCG basic - Red periphery | CresRed - Black (no change) | CresRed basic - Green | CP Red - Black (no change) |
| R Dye - Black (no change) | TB - Black (no change) | TB basic - Black (no change) | MeOr - Black (no change) | MeOr basic - Black (no change) | CP Red basic - Yellow Periphery and Purple Center |

(Analyte: Formic Acid 340 ppb)

| | | | | | |
|---|---|---|---|---|---|
| SnTPPCl₂ - Black (no change) | CoTPP - Black (no change) | CrTPPCl - Black (no change) | MnTPPCl - Black (no change) | FeTPPCl - Black (no change) | CuTPP - Black (no change) |
| AgTPP - Black (no change) | NiTPP - Black (no change) | InTPPCL - Black (no change) | IrTPPCl - Black (no change) | ZnTPP - Black (no change) | FeTFPPCl - Black (no change) |
| ZnSi₆PP - Black (no change) | ZnSi₇OHPP - Black (no change) | ZnSi₈PP - Black (no change) | H₂TPP - Black (no change) | H₂FPP - Black (no change) | Alizarin basic - Green and Purple |
| Me Red - Black (no change) | BCP - Yellow | BCP basic - White | BTB - Black (no change) | BTB basic - Yellow | Ph Red basic - Green |
| Nile Red - Black (no change) | BCG - Red | BCG basic - Red and Purple | CresRed - Black (no change) | CresRed basic - Light Green | CP Red - Green |
| R Dye - Black (no change) | TB - Black (no change) | TB basic - Black (no change) | MeOr - Blue | MeOr basic - Purple | CP Red basic - White |

(Analyte: Formic Acid 680 ppb)

| | | | | | |
|---|---|---|---|---|---|
| SnTPPCl₂ - Black (no change) | CoTPP - Black (no change) | CrTPPCl - Black (no change) | MnTPPCl - Black (no change) | FeTPPCl - Black (no change) | CuTPP - Black (no change) |
| AgTPP - Black (no change) | NiTPP - Black (no change) | InTPPCL - Black (no change) | IrTPPCl - Black (no change) | ZnTPP - Black (no change) | FeTFPPCl - Black (no change) |
| ZnSi₆PP - Black (no change) | ZnSi₇OHPP - Black (no change) | ZnSi₈PP - Black (no change) | H₂TPP - Black (no change) | H₂FPP - Black (no change) | Alizarin basic - Green and Purple |
| Me Red - Black (no change) | BCP - Yellow | BCP basic - White | BTB - Black (no change) | BTB basic - Red Periphery and Yellow Center | Ph Red basic - Green |
| Nile Red - Black (no change) | BCG Red and Purple | BCG basic - Red and Purple | CresRed - Black (no change) | CresRed basic - Green | CP Red - Black (no change) |
| R Dye - Black (no change) | TB - Black (no change) | TB basic - Black (no change) | MeOr - Light blue | MeOr basic - Purple | CP Red basic - White |

(Analyte: Acetic Acid 170 ppb)

| | | | | | |
|---|---|---|---|---|---|
| SnTPPCl₂ - Black (no change) | CoTPP - Black (no change) | CrTPPCl - Black (no change) | MnTPPCl - Black (no change) | FeTPPCl - Black (no change) | CuTPP - Black (no change) |
| AgTPP - Black (no change) | NiTPP - Black (no change) | InTPPCL - Black (no change) | IrTPPCl - Black (no change) | ZnTPP - Black (no change) | FeTFPPCl - Black (no change) |
| ZnSi₆PP - Black (no change) | ZnSi₇OHPP - Black (no change) | ZnSi₈PP - Black (no change) | H₂TPP - Black (no change) | H₂FPP - Black (no change) | Alizarin basic - Black (no change) |
| Me Red - Black (no change) | BCP - Red | BCP basic - Orange | BTB - Black (no change) | BTB basic - Red | Ph Red basic - Black (no change) |

TABLE 12-continued (Summarizing the Dyes and Color Changes in FIG. 17, i.e. "Dye - Difference Map Color")

| | | | | | |
|---|---|---|---|---|---|
| Nile Red - Black (no change) | BCG - Purple and Orange | BCG basic - Purple Orange | CresRed - Black (no change) | CresRed basic - Black (no change) | CP Red. - Black (no change) |
| R Dye - Black (no change) | TB - Black (no change) | TB basic - Black (no change) | MeOr - Black (no change) | MeOr basic - Black (no change) | CP Red basic - Black (no change) |

(Analyte: Acetic Acid 250 ppb)

| | | | | | |
|---|---|---|---|---|---|
| SnTPPCl$_2$ - Black (no change) | CoTPP - Black (no change) | CrTPPCl - Black (no change) | MnTPPCl - Black (no change) | FeTPPCl - Black (no change) | CuTPP - Black (no change) |
| AgTPP - Black (no change) | NiTPP - Black (no change) | InTPPCL - Black (no change) | IrTPPCl - Black (no change) | ZnTPP - Black (no change) | FeTFPPCl - Black (no change) |
| ZnSi$_6$PP - Black (no change) | ZnSi$_7$OHPP - Black (no change) | ZnSi$_8$PP - Black (no change) | H$_2$TPP - Black (no change) | H$_2$FPP - Black (no change) | Alizarin basic - Black (no change) |
| Me Red - Black (no change) | BCP - Yellow with Red Center | BCP basic - Red | BTB - Black (no change) | BTB basic - Red | Ph Red basic - Green |
| Nile Red - Black (no change) | BCG - Orange | BCG basic - Red and Purple | CresRed - Black (no change) | CresRed basic - Black (no change) | CP Red - Black (no change) |
| R Dye - Black (no change) | TB - Black (no change) | TB basic - Black (no change) | MeOr - Black (no change) | MeOr basic - Black (no change) | CP Red basic - White |

(Analyte: Acetic Acid 340 ppb)

| | | | | | |
|---|---|---|---|---|---|
| SnTPPCl$_2$ - Black (no change) | CoTPP - Black (no change) | CrTPPCl - Black (no change) | MnTPPCl - Black (no change) | FeTPPCl - Black (no change) | CuTPP - Black (no change) |
| AgTPP - Black (no change) | NiTPP - Black (no change) | InTPPCL - Black (no change) | IrTPPCl - Black (no change) | ZnTPP - Black (no change) | FeTFPPCl - Black (no change) |
| ZnSi$_6$PP - Black (no change) | ZnSi$_7$OHPP - Black (no change) | ZnSi$_8$PP - Black (no change) | H$_2$TPP - Black (no change) | H$_2$FPP - Black (no change) | Alizarin basic - Black (no change) |
| Me Red - Black (no change) | BCP - Yellow | BCP basic - Yellow | BTB - Black (no change) | BTB basic - Ornage | Ph Red basic - Green |
| Nile Red - Black (no change) | BCG - Faint Orange and Purple | BCG basic - Purple | CresRed - Black (no change) | CresRed basic - Green | CP Red - Black (no change) |
| R Dye - Black (no change) | TB - Black (no change) | TB basic - Black (no change) | MeOr - Black (no change) | MeOr basic - Black (no change) | CP Red basic - White |

(Analyte: Acetic Acid 650 ppb)

| | | | | | |
|---|---|---|---|---|---|
| SnTPPCl$_2$ - Black (no change) | CoTPP - Black (no change) | CrTPPCl - Black (no change) | MnTPPCl - n Black (no change) | FeTPPCl - Black (no change) | CuTPP - Black (no change) |
| AgTPP - Black (no change) | NiTPP - Black (no change) | InTPPCL - Black (no change) | IrTPPCl - Black (no change) | ZnTPP - Black (no change) | FeTFPPCl - Black (no change) |
| ZnSi$_6$PP - Black (no change) | ZnSi$_7$OHPP - Black (no change) | ZnSi$_8$PP - Black (no change) | H$_2$TPP - Black (no change) | H$_2$FPP - Black (no change) | Alizarin basic - Faint Green |
| Me Red - Black (no change) | BCP - Yellow and Orange) | BCP basic - Faint Yellow | BTB - Orange | BTB basic - Yellow | Ph Red basic - Green |
| Nile Red - Black (no change) | BCG - Black (no change) | BCG basic - Purple | CresRed - Black (no change) | CresRed basic - White | CP Red - Faint Green |
| R Dye - Black (no change) | TB - Black (no change) | TB basic - Black (no change) | MeOr - Black (no change) | MeOr basic - Green | CP Red basic - White |

TABLE 12-continued (Summarizing the Dyes and Color Changes in FIG. 17, i.e. "Dye - Difference Map Color")

(Analyte: Iso-Valeric Acid 280 ppb)

| | | | | | |
|---|---|---|---|---|---|
| SnTPPCl$_2$ - Black (no change) | CoTPP - Black (no change) | CrTPPCl - Black (no change) | MnTPPCl - Black (no change) | FeTPPCl - Black (no change) | CuTPP - Black (no change) |
| AgTPP - Black (no change) | NiTPP - Black (no change) | InTPPCL - Black (no change) | IrTPPCl - Black (no change) | ZnTPP - Black (no change) | FeTFPPC - Black (no change) |
| ZnSi$_6$PP - Black (no change) | ZnSi$_7$OHPP - Black (no change) | ZnSi$_8$PP - Black (no change) | H$_2$TPP - Black (no change) | H$_2$FPP - Black (no change) | Alizarin basic - Black (no change) |
| Me Red - Black (no change) | BCP - Red Black (no change) | BCP basic - Faint Red | BTB - Black (no change) | BTB basic - Orange | Ph Red basic - Orange |
| Nile Red - Black (no change) | BCG - Faint Purple Periphery | BCG basic - Red Periphery | CresRed - Black (no change) | CresRed basic - Dark Green | CP Red - Black (no change) |
| R Dye - Black (no change) | TB - Red and Purple Periphery | TB basic - Red Periphery | MeOr - Green Center | MeOr basic - Green Periphery | CP Red basic - Green Periphery |

(Analyte: Iso-Valeric 420 ppb)

| | | | | | |
|---|---|---|---|---|---|
| SnTPPCl$_2$ - Black (no change) | CoTPP - Black (no change) | CrTPPCl - Black (no change) | MnTPPCl - Black (no change) | FeTPPCl - Black (no change) | CuTPP - Black (no change) |
| AgTPP - Black (no change) | NiTPP - Black (no change) | InTPPCL - Black (no change) | IrTPPCl - Black (no change) | ZnTPP - Black (no change) | FeTFPPCl - Black (no change) |
| ZnSi$_6$PP - Black (no change) | ZnSi$_7$OHPP - Black (no change) | ZnSi$_8$PP - Black (no change) | H$_2$TPP - Black (no change) | H$_2$FPP - Black (no change) | Alizarin basic - Black (no change) |
| Me Red - Black (no change) | BCP - Red | BCP basic - Faint Green and orange | BTB - Black (no change) | BTB basic - Orange and Yellow | Ph Red basic - Faint Orange and Green |
| Nile Red - Black (no change) | BCG - Orange | BCG basic - Orange Periphery | CresRed - Black (no change | CresRed basic - Green | CP Red - Black (no change) |
| R Dye - Black (no change) | TB - Black (no change) | TB basic - Black (no change) | MeOr - Green | MeOr basic - Green | CP Red basic - Green |

(Analyte: Iso-Valeric Acid 850 ppb)

| | | | | | |
|---|---|---|---|---|---|
| SnTPPCl$_2$ - Faint blue | CoTPP - Faint Purple | CrTPPCl - Faint Purple | MnTPPCl - Faint Purple | FeTPPCl - Faint Purple | CuTPP - Black (no change) |
| AgTPP - Faint Blue | NiTPP - Black (no change) | InTPPCL - Faint Pink | IrTPPC1 - Black (no change) | ZnTPP - Black (no change) | FeTFPPCl - Black (no change) |
| ZnSi$_6$PP - Faint Blue | ZnSi$_7$OHPP Faint Blue | ZnSi$_8$PP - Black (no change) | H$_2$TPP - Faint Blue | H$_2$FPP - Black (no change) | Alizarin basic - Black (no change) |
| Me Red - Black (no change) | BCP - White and Red | BCP basic - Yellow and Red | BTB - Blue and Red | BTB basic - Red and Yellow | Ph Red basic - Yellow and Red |
| Nile Red - Black (no change) | BCG - White, Red and Blue | BCG basic - White and Red | CresRed - Purple Periphery | CresRed basic - Light Green | CP Red - Faint Orange |
| R Dye - Faint Red | TB - Light Blue Periphery | TB basic - Purple Periphery and Red Center | MeOr - Green and Blue | MeOr basic - Light Green | CP Red basic - Light Green |

(Analyte: Iso-Valeric Acid 1700 ppb)

| | | | | | |
|---|---|---|---|---|---|
| SnTPPCl$_2$ - Black (no change) | CoTPP - Black (no change) | CrTPPCl - Black (no change) | MnTPPCl - Black (no change) | FeTPPCl - Black (no change) | CuTPP - Black (no change) |
| AgTPP - Black (no change) | NiTPP - Black (no change) | InTPPCL - Black (no change) | IrTPPCl - Black (no change) | ZnTPP - Black (no change) | FeTFPPCl - Black (no change) |

TABLE 12-continued (Summarizing the Dyes and Color Changes in FIG. 17, i.e. "Dye - Difference Map Color")

| | | | | | |
|---|---|---|---|---|---|
| $ZnSi_6PP$ - Black (no change) | $ZnSi_7OHPP$ - Black (no change) | $ZnSi_8PP$ - Black (no change) | $H_2TPP$ - Black (no change) | $H_2FPP$ - Black (no change) | Alizarin basic - Faint Purple |
| Me Red - Black (no change) | BCP - Red | BCP basic - White | BTB - Black (no change) | BTB basic - White | Ph Red basic - White and Purple |
| Nile Red - Black (no change) | BCG - Red and Purple | BCG basic - White, Red, and Purple | CresRed - Black (no change) | CresRed basic - White | CP Red - Black (no change) |
| R Dye - Black (no change) | TB - Black (no change) | TB basic - Faint Red | MeOr - Black (no change) | MeOr basic - Faint Green | CP Red basic - Green |
| (Analyte: 3-Methyl-2-hexenoic Acid 12 ppb) | | | | | |
| $SnTPPCl_2$ - Black (no change) | CoTPP - Black (no change) | CrTPPCl - Black (no change) | MnTPPCl - Black (no change) | FeTPPCl - Black (no change) | CuTPP - Black (no change) |
| AgTPP - Black (no change) | NiTPP - Black (no change) | InTPPCL - Black (no change) | IrTPPCl - Black (no change) | ZnTPP - Black (no change) | FeTFPPCl - Black (no change) |
| $ZnSi_6PP$ - Black (no change) | $ZnSi_7OHPP$ - Black (no change) | $ZnSi_8PP$ - Black (no change) | $H_2TPP$ - Black (no change) | $H_2FPP$ - Black (no change) | Alizarin basic - Black (no change) |
| Me Red - Black (no change) | BCP - Faint Purple | BCP basic - White and Purple | BTB - Black (no change) | BTB basic - Red | Ph Red basic - Purple and Green |
| Nile Red - Black (no change) | BCG - Faint Red and Purple | BCG basic - Faint White and Purple | CresRed - Black (no change) | CresRed basic - Light Blue and Green | CP Red - Black (no change) |
| R Dye - Black (no change) | TB - Black (no change) | TB basic - Black (no change) | MeOr - Black (no change) | MeOr basic - Blue and Green | CP Red basic - Green |

Figure 18:
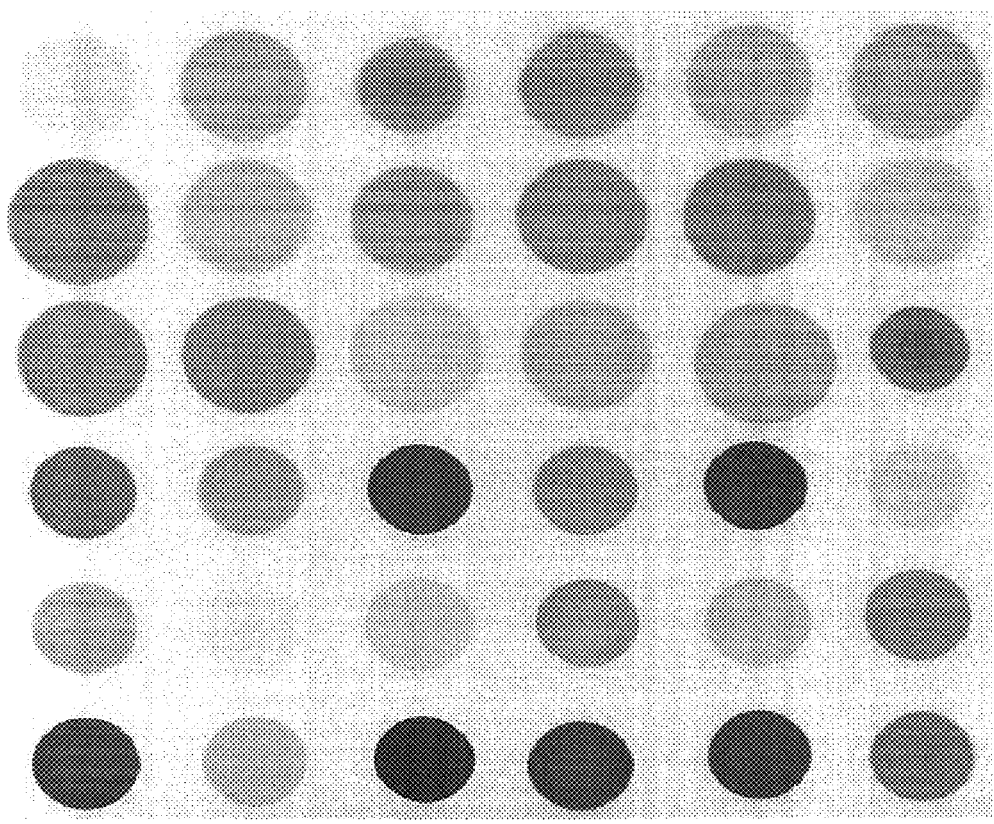
FIG. 18 illustrates a preferred array containing illustrative examples of porphyrin, metalloporphyrin, acid-base indicator, and solvatochromatic dyes.

FIG. 18 illustrates a preferred array containing illustrative examples of porphyrin, metalloporphyrin, acid-base indicator, and solvatochromatic dyes. Typical sizes of the array can range from 0.5 mm to 2 cm on a side. Linear, hexagonal or rectangular arrays are also easily used. From left to right and top to bottom the identities and colors of the dyes used in the illustrative example of FIG. 18 are listed in Table 13 as follows (the exact colors depend, among other things, upon scanner setting).

TABLE 13

(Summarizing the Dyes and Colors in FIG. 18, i.e., "Dye - Color")

| | | | | | |
|---|---|---|---|---|---|
| $SnTPPCl_2$- Light Green | CoTPP - Tan | CrTPPCl - Green with Dark Green Center | MnTPPCl - Green | FeTPPCl - Light Green | CuTPP - Light Pink |
| $Zn(C_3F_7)_4P$ - Gray | $ZnF_2PP$ - Light Pink | InTPPCl - Reddish Beige | ZnTMP - Pink | ZnTPP - Salmon | FeTFPPCl - Beige |
| $ZnSi_6PP$ - Pink | $ZnSi_7OHPP$ - Pink | $ZnSi_8PP$ - Light Pink | $H_2TPP$ - Light Reddish Beige | $H_2FPP$ - Greenish Yellow | Neutral Red Pink with Brown Center |
| Methyl Red - Orange | Disperse Orange 25 - Pinkish Orange | Rosolic Acid - Red | Fat Brown RR - Dark | Cyanidin Chloride - Reddish Brown | Metanil Yellow - Light Yellow |
| Nile Red - Light Purple | Mordant Orange 1 - Light Yellow | 3,6-Acridineamine Yellow | Bromocresol Green - Dark Yellow | Azodipyridine - Yellow | Rosaniline - Pink |
| Reichardt's Dye - Teal | Acridine Orange Base - Yellow | Crystal Violet - Dark Blue | Thymol Blue -Purple | Congo Red - Dark Red | Malachite Green Carbinol base - Light Blue |

Note:
DOW CORNING 704 silicone diffusion pump fluid (Molecular Weight: 484.82, Density: 1.070, CAS Number: 3982-82-9) was added to all porphyrin solutions: 40 μl/ml.

where

SnTPPCl$_2$ is 5,10,15,20-Tetraphenyl-21H,23H-porphine Tin (IV) Dichloride
Molecular Formula: C$_{44}$H$_{28}$SnCl$_2$N$_4$
Molecular Weight: 802
CAS: 26334-85-0;

CoTPP is 5,10,15,20-Tetraphenyl-21H,23H-porphine Cobalt(II)
Molecular Formula: C$_{44}$H$_{28}$CoN$_4$
Molecular Weight: 671
CAS: 14172-90-8;

CrTPPCl is 5,10,15,20-Tetraphenyl-21H,23H-porphine Chromium(III) Chloride
Molecular Formula: C$_{44}$H$_{28}$CrClN$_4$
Molecular Weight: 700
CAS: 28110-70-5;

MnTPPCl is 5,10,15,20-Tetraphenyl-21H,23H-porphine Manganese(III) Chloride
Molecular Formula: C$_{44}$H$_{28}$ClMnN$_4$
Molecular Weight: 703
CAS: 32195-55-4;

FeTPPCl is 5,10,15,20-Tetraphenyl-21H,23H-porphine Iron (III) Chloride
Molecular Formula: C$_{44}$H$_{28}$ClFeN$_4$
Molecular Weight: 704
CAS: 16456-81-8;

CuTPP is 5,10,15,20-Tetraphenyl-21H,23H-porphine Copper(II)
Molecular Formula: C$_{44}$H$_{28}$CuN$_4$
Molecular Weight: 676
CAS: 14172-91-9;

Zn(C$_3$F$_7$)$_4$P is Meso tetra(heptafluoropropyl)porphine Zinc (II)
Molecular Formula: C$_{32}$H$_8$ZnF$_{28}$N$_4$
Molecular Weight: 1044;

ZnF$_2$PP is 5,10,15,20-Tetrakis(2,6-difluorophenyl)-21H,23H-porphine Zinc(II)
Molecular Formula: C$_{44}$H$_{20}$F$_8$N$_4$Zn
Molecular Weight: 820;

InTPPCl is 5,10,15,20-Tetraphenyl-21H,23H-porphine Indium(III) Chloride
Molecular Formula: C$_{44}$H$_{28}$ClInN$_4$
Molecular Weight: 763;

ZnTMP is 5,10,15,20-Tetrakis(2,4,6-trimethylphenyl)-21H,23H-porphine Zinc(II)
Molecular Formula: C$_{56}$H$_{52}$N$_4$Zn
Molecular Weight: 846
CAS: 104025-54-9;

ZnTPP is 5,10,15,20-Tetraphenyl-21H,23H-porphine Zinc (II)
Molecular Formula: C$_{44}$H$_{28}$N$_4$Zn
Molecular Weight: 678
CAS: 14074-80-7;

FeTFPPCl is 5,10,15,20-Tetrakis(pentafluorophenyl)-21H,23H-porphine Iron(III) Chloride
Molecular Formula: C$_{44}$H$_8$ClF$_{20}$FeN$_4$
Molecular Weight: 1063.85
CAS: 36965-71-6;

ZnSi$_6$PP is 5(phenyl)-10,15,20-trikis(2',6'-disilyloxyphenyl)porphyrinatozinc(II)
Molecular Formula: ZnC$_{80}$H$_{112}$O$_6$N$_4$Si$_6$
Molecular Weight: 1458;

ZnSi$_7$OHPP is 5,10,15-trikis(2',6'-disilyloxyphenyl)-20-(2'-hydroxy-6'-silyloxyphenyl)porphyrinatozinc(II)
Molecular Formula: ZnC$_{86}$H$_{126}$O$_8$N$_4$Si$_7$
Molecular Weight: 1604;

ZnSi$_8$PP is 5,10,15,20-tetrakis(2',6'-disilyloxyphenyl)porphyrinatozinc(II)
Molecular Formula: ZnC$_{92}$H$_{140}$O$_8$N$_4$Si$_8$
Molecular Weight: 1718;

H$_2$TPP is 5,10,15,20-Tetraphenyl-21H,23H-porphine
Molecular Formula: C$_{44}$H$_{30}$N$_4$
Molecular Weight: 614.75
CAS: 917-23-7;

H$_2$FPP is 5,10,15,20-Tetrakis(pentafluorophenyl)-21H,23H-porphine
Molecular Formula: C$_{44}$H$_{10}$F$_{20}$N$_4$
Molecular Weight: 974.57
CAS: 25440-14-6;

Azodipyridine is 6'-Butoxy-2,6-diamino-3,3'-azodipyridine
Molecular Formula: C$_{14}$H$_{18}$N$_6$O
Molecular Weight: 286.34
CAS: 617-19-6;

Rosaniline is Para-Rosaniline Base
Molecular Formula: C$_{19}$H$_{19}$N$_3$O
Molecular Weight: 305.4
CAS: 25620-78-4

Figure 19:
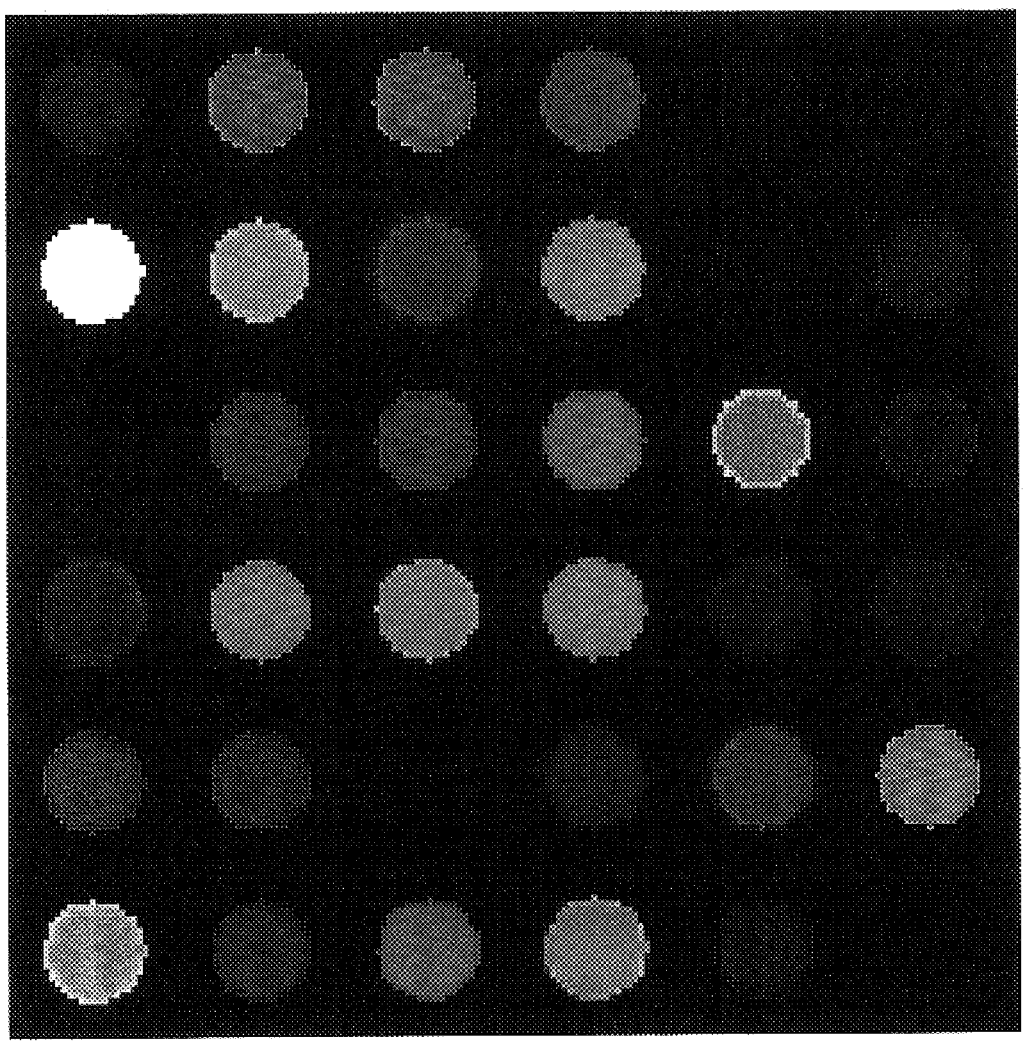
FIG. 19 illustrates the response of the array described in FIG. 18 to acetone.

FIG. 19 illustrates the response of the array described in FIG. 18 to acetone. As shown in FIG. 18 and summarized in Table 14 below, the color changes of each dye in response to aceteone are as follows (the exact colors depend, among other things, upon scanner settings). The color changes are derived simply by comparing the before exposure and after exposure colors and subtracting the two images (i.e., the absolute value of the difference of the red values becomes the new red value in the color difference map; etc. for green values and blue values). If there is no change in the red, green, and blue color values of a dye in the after-exposure image, then the color difference map will show black (i.e., red value=green value=blue value=0).

TABLE 14

(Summarizing the Dyes and Colors in FIG. 19, i.e., "Dye - Color")

| | | | | | |
|---|---|---|---|---|---|
| SnTPPCl$_2$ - Reddish Brown | CoTPP - Lavender | CrTPPCl - Gray | MnTPPCl Pink | FeTPPCl - Black (no change) | CuTPP - Black (no change) |
| AgTPP - White | NiTPP - Light Teal | InTPPCL - Blue | IrTPPCl - Light Green | ZnTPP - Black (no change) | FeTFPPCl - Dark Dark Cobalt |

TABLE 14-continued (Summarizing the Dyes and Colors in FIG. 19, i.e., "Dye - Color")

| | | | | | |
|---|---|---|---|---|---|
| ZnSi$_6$PP - Black (no change) | ZnSi$_7$OHPP - Aqua | ZnSi$_8$PP - Dark Teal | H$_2$TPP - Green | H$_2$FPP - White Periphery and Blue Center | Alizarin basic - Dark Purple |
| Me Red - Dark Blue | BCP - Green | BCP basic - Light Green | BTB - Light Green | BTB basic - Dark Blue | Ph Red basic - Royal Blue |
| Nile Red - Olive | BCG - Tan | BCG basic - Black (no change) | CresRed - Dark Pink | CresRed basic - Blue | CP Red - Gold |
| R Dye - Light Pink | TB - Brown | TB basic - Green | MeOr - Light Green | MeOr basic - Dark Blue | CP Red basic - Black (no change) |

Many modifications and variations may be made in the techniques and structures described and illustrated herein without departing from the spirit and scope of the present invention. Accordingly, the techniques and structures described and illustrated herein should be understood to be illustrative only and not limiting upon the scope of the present invention.

What is claimed is:

1. An artificial nose comprising an array, the array comprising at least a first dye and a second dye deposited directly onto a single support in a predetermined pattern combination, the combination of the dyes in the array having a distinct and direct spectral absorbance or reflectance response to distinct analytes, wherein the first dye is selected from the group consisting of porphyrin, chlorin, chlorophyll, phthalocyanine, and salen and their metal complexes, and the second dye is distinct from the first dye and selected from the group of dyes consisting of acid-base indicator dyes and solvatochromic dyes.

2. The artificial nose of claim 1 wherein the first dye is a metalloporphyrin.

3. The artificial nose of claim 1 wherein the second dye is an acid-base indicator dye.

4. The artificial nose of claim 1 wherein the second dye is a solvatochromic dye.

5. The artificial nose of claim 1 wherein the second dye is selected from the group consisting of Chlorphenol Red, Bromocresol Green, Bromocresol Purple, Bromothymol Blue, Phenol Red, Thymol Blue, Cresol Red, Alizarin, Mordant Orange, Methyl Orange, Methyl Red, Reichardt's Dye, Nile Red, Congo Red, Victoria Blue B, Eosin Blue, Fat Brown B, Benzopurpurin 4B, Phloxine B, Orange G, Metanil Yellow, Naphthol Green B, Methylene Blue, Safranine O, Methylene Violet 3RAX, Sudan Orange G, Morin Hydrate, Neutral Red, Disperse Orange 25, Rosolic Acid, Fat Brown RR, Cyanidin chloride, 3,6-Acridineamine, 6'Butoxy2,6di-amino3,3'-azodipyridine, para-Rosaniline Base, Acridine Orange Base, Crystal Violet, and Malachite Green Carbinol Base.

6. The artificial nose of claim 1 wherein the first dye is a porphyrin and has a periphery and a superstructure bonded to the periphery.

7. A method of detecting an analyte comprising the steps of: forming an array of at least a first dye and a second dye deposited directly onto a single support in a predetermined pattern combination, the combination of the dyes in the array having a distinct and direct spectral absorbance or reflectance response to distinct analytes wherein the first dye is selected from the group consisting of porphyrin, chlorin, chlorophyll, phthalocyanine, and salen and their metal complexes, and the second dye is distinct from the first dye and selected from the group of acid-base indicator dyes and solvatochromic dyes, subjecting the array to an analyte, inspecting the array for a distinct and direct spectral absorbance or reflectance response, and correlating the distinct and direct spectral response to the presence of the analyte.

8. The method of claim 7 wherein the first dye is a metalloporphyrin.

9. The method of claim 7 wherein the second dye is an acid-base indicator dye.

10. The method of claim 7 wherein the second dye is a solvatochromic dye.

11. The method of claim 7 wherein the second dye is selected from the group consisting of Chlorphenol Red, Bromocresol Green, Bromocresol Purple, Bromothymol Blue, Phenol Red, Thymol Blue, Cresol Red, Alizarin, Mordant Orange, Methyl Orange, Methyl Red, Reichardt's Dye, Nile Red, Congo Red, Victoria Blue B, Eosin Blue, Fat Brown B, Benzopurpurin 4B, Phloxine B, Orange G, Metanil Yellow, Naphthol Green B, Methylene Blue, Safranine 0, Methylene Violet 3RAX, Sudan Orange G, Morin Hydrate, Neutral Red, Disperse Orange 25, Rosolic Acid, Fat Brown RR, Cyanidin chloride, 3,6-Acridineamine, 6'-Butoxy-2,6-diamino-3,3'-azodipyridine, para-Rosaniline Base, Acridine Orange Base, Crystal Violet, and Malachite Green Carbinol Base.

12. The method of claim 7 wherein the first dye is a porphyrin and has a periphery and a superstructure bonded to the periphery.

13. An artificial tongue comprising an array, the array comprising at least a first dye and a second dye deposited directly onto a single support in a predetermined pattern combination, the combination of the dyes in the array having a distinct and direct spectral absorbance or reflectance response to distinct analytes in solution or liquid analytes, or analytes in a solid or solid analytes, wherein the first dye is selected from the group consisting of porphyrin, chlorin, chlorophyll, phthalocyanine, and salen and their metal complexes, and the second dye is distinct from the first dye and selected from the group of dyes consisting of acid-base indicator dyes and solvatochromic dyes.

14. The artificial tongue of claim 13 wherein the first dye is a metalloporphyrin.

15. The artificial tongue of claim 13 wherein the second dye is an acid-base indicator dye.

16. The artificial tongue of claim 13 wherein the second dye is a solvatochromic dye.

17. The artificial tongue of claim 13 wherein the second dye is selected from the group consisting of Chlorphenol Red, Bromocresol Green, Bromocresol Purple, Bromothymol Blue, Phenol Red, Thymol Blue, Cresol Red, Alizarin, Mordant Orange, Methyl Orange, Methyl Red, Reichardt's Dye, Nile Red, Congo Red, Victoria Blue B, Eosin Blue, Fat Brown B, Benzopurpurin 4B, Phloxine B, Orange G, Metanil Yellow, Naphthol Green B, Methylene Blue, Safranine O, Methylene Violet 3RAX, Sudan Orange G, Morin Hydrate, Neutral Red, Disperse Orange 25, Rosolic Acid, Fat Brown RR, Cyanidin chloride, 3,6-Acridineamine, 6'-Butoxy2,6diamino-3,3'-azodipyridine, para-Rosaniline Base, Acridine Orange Base, Crystal Violet, and Malachite Green Carbinol Base.

18. The artificial tongue of claim 13 wherein the first dye is a porphyrin and has a periphery and a superstructure bonded to the periphery.

19. The artificial nose of claim 1 further comprising a low volatility liquid.

20. The method of claim 7 further comprising the step of adding a low volatility liquid to the array.

21. The artificial tongue of claim 13 further comprising a low volatility liquid.

22. The method of claim 7 further comprising the step of forming a table of responses of the array to a plurality of distinct analytes.

* * * * *